US009028821B2

(12) United States Patent
Hasegawa et al.

(10) Patent No.: US 9,028,821 B2
(45) Date of Patent: May 12, 2015

(54) METHOD OF TREATING AN INFLAMMATORY DISEASE COMPRISING ADMINISTERING AN NR 10 ANTIBODY ANTAGONIST

(75) Inventors: Masakazu Hasegawa, Shizuoka (JP); Hidetomo Kitamura, Shizuoka (JP); Hideki Adachi, Shizuoka (JP); Keiko Kasutani, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 90 days.

(21) Appl. No.: 12/303,684

(22) PCT Filed: Jun. 8, 2007

(86) PCT No.: PCT/JP2007/061625
§ 371 (c)(1),
(2), (4) Date: May 27, 2009

(87) PCT Pub. No.: WO2007/142325
PCT Pub. Date: Dec. 13, 2007

(65) Prior Publication Data
US 2010/0055092 A1 Mar. 4, 2010

(30) Foreign Application Priority Data
Jun. 8, 2006 (JP) ................................. 2006-160096

(51) Int. Cl.
*A61K 39/395* (2006.01)
*A61P 17/04* (2006.01)
*A61P 17/00* (2006.01)
*A61P 29/00* (2006.01)
*A61P 19/02* (2006.01)
*C07K 16/28* (2006.01)
*A61K 39/00* (2006.01)

(52) U.S. Cl.
CPC ....... *C07K 16/2866* (2013.01); *A61K 2039/505* (2013.01); *C07K 2316/96* (2013.01); *C07K 2317/21* (2013.01); *C07K 2317/24* (2013.01); *C07K 2317/565* (2013.01); *C07K 2317/622* (2013.01); *C07K 2319/00* (2013.01); *C07K 2317/52* (2013.01)

(58) Field of Classification Search
None
See application file for complete search history.

(56) References Cited

U.S. PATENT DOCUMENTS

| | | | |
|---|---|---|---|
| 5,455,030 A | 10/1995 | Ladner et al. | |
| 6,018,032 A | 1/2000 | Koike et al. | |
| 6,019,967 A | 2/2000 | Breton et al. | |
| 6,642,360 B2 | 11/2003 | Filvaroff et al. | |
| 6,747,137 B1 | 6/2004 | Weinstock et al. | |
| 6,756,481 B2 | 6/2004 | Chirica et al. | |
| 7,045,595 B2 | 5/2006 | Maeda et al. | |
| 7,250,168 B2 | 7/2007 | Light et al. | |
| 7,411,041 B2 | 8/2008 | Chirica et al. | |
| 7,482,440 B2 | 1/2009 | Maeda et al. | |
| 8,431,127 B2 | 4/2013 | Higuchi et al. | |
| 8,575,317 B2 | 11/2013 | Kuramochi et al. | |
| 2003/0082734 A1 | 5/2003 | Dowling et al. | |
| 2003/0125520 A1 | 7/2003 | Maeda et al. | |
| 2003/0215838 A1* | 11/2003 | Sprecher et al. ................... 435/6 |
| 2003/0224487 A1 | 12/2003 | Sprecher et al. | |
| 2004/0142422 A1* | 7/2004 | Sprecher et al. ............. 435/69.1 |
| 2004/0223970 A1 | 11/2004 | Afar et al. | |
| 2006/0106201 A1 | 5/2006 | Maeda et al. | |
| 2006/0121022 A1 | 6/2006 | Koga et al. | |
| 2006/0166284 A1 | 7/2006 | Light et al. | |
| 2006/0182743 A1* | 8/2006 | Bilsborough ............... 424/143.1 |
| 2007/0160611 A1 | 7/2007 | Yao et al. | |
| 2007/0203328 A1 | 8/2007 | Maeda et al. | |
| 2008/0019985 A1 | 1/2008 | Light et al. | |
| 2008/0020965 A1 | 1/2008 | Light et al. | |
| 2008/0125579 A1 | 5/2008 | Owens et al. | |
| 2008/0219971 A1 | 9/2008 | Smith et al. | |
| 2009/0023660 A1 | 1/2009 | Maeda et al. | |
| 2009/0029484 A1 | 1/2009 | Maeda et al. | |
| 2009/0105457 A1 | 4/2009 | Maeda et al. | |
| 2009/0105458 A1 | 4/2009 | Maeda et al. | |
| 2009/0105459 A1 | 4/2009 | Maeda et al. | |

(Continued)

FOREIGN PATENT DOCUMENTS

AU 2006/214404 8/2006
AU 2007/249713 11/2007

(Continued)

OTHER PUBLICATIONS

Phillips, A., J Pharm Pharmacology 53: 1169-1174, 2001.*
Vidal et al. 2005. European Journal of Cancer. 41: 2812-2818.*
Pirollo et al, 2008. Cancer Res. 68(5): 1247-1250.*
Benjamini et al, 1991. Immunology: A Short Course, 2nd edition, p. 40 only.*
Vaughan et al., "Human antibodies by design," Nature Biotechnology, 16(6):535-539 (1998).
Fish & Richardson P.C Amendment in Reply to Action dated Jun. 4, 2009 in U.S. Appl. No. 11/595,320, filed Dec. 3, 2009, 13 pages.
Fish & Richardson P.C. Reply to Restriction Requirement dated Oct. 9, 2009 in U.S. Appl. No. 12/205,799, filed Nov. 4, 2009, 1 page.

(Continued)

*Primary Examiner* — Zachary Howard
(74) *Attorney, Agent, or Firm* — Fish & Richardson P.C.

(57) ABSTRACT

The present inventors obtained, from a phage library of human antibodies, an anti-mouse NR 10 neutralizing antibody-expressing BM095 clone that shows a strong proliferation-suppressing activity in an IL-31-dependent Ba/F3 cell proliferation assay system. When this anti-mouse NR 10 neutralizing antibody was administered to NC/Nga mice, a model of atopic dermatitis which is a mouse model of chronic dermatitis that arises as a result of repeated applications of picryl chloride, a mouse model of rheumatoid arthritis, and a mouse model of osteoarthritis, a significant effect of symptom suppression was observed. This revealed that the anti-NR 10 neutralizing antibody is indeed effective as a therapeutic agent for inflammatory diseases. In addition, the present inventors successfully obtained an anti-human NR 10 neutralizing antibody, providing extremely useful therapeutic agents with practical clinical applications.

20 Claims, 13 Drawing Sheets

(56) References Cited

U.S. PATENT DOCUMENTS

| | | |
|---|---|---|
| 2009/0111972 A1 | 4/2009 | Maeda et al. |
| 2010/0016552 A1 | 1/2010 | Maeda et al. |
| 2010/0240096 A1 | 9/2010 | Maeda et al. |
| 2010/0240145 A1 | 9/2010 | Maeda et al. |
| 2010/0285030 A1 | 11/2010 | Bowdish et al. |
| 2010/0310556 A1 | 12/2010 | Higuchi et al. |
| 2011/0229459 A1 | 9/2011 | Kuramochi et al. |
| 2014/0039165 A1 | 2/2014 | Kuramochi et al. |

FOREIGN PATENT DOCUMENTS

| | | |
|---|---|---|
| AU | 2007/255753 | 12/2007 |
| AU | 2008332271 | 6/2009 |
| CA | 2 594 490 | 8/2006 |
| CA | 2 633 439 | 11/2007 |
| CA | 2 636 288 | 12/2007 |
| CA | 2 708 065 | 6/2009 |
| CA | 2 708 532 | 6/2009 |
| EA | 009026 | 10/2007 |
| EP | 0 411 946 | 2/1991 |
| EP | 0 931 646 | 7/1999 |
| EP | 1 088 831 | 4/2001 |
| EP | 1 188 830 | 3/2002 |
| EP | 2 047 863 | 4/2009 |
| EP | 2 236 604 | 10/2010 |
| EP | 2 241 332 | 10/2010 |
| JP | 2005-532045 | 10/2005 |
| RU | 2180854 | 3/2002 |
| RU | 2010127292 | 1/2012 |
| TW | 200810778 | 3/2008 |
| TW | 200932266 | 8/2009 |
| WO | WO 94/10354 | 5/1994 |
| WO | WO 94/12215 | 6/1994 |
| WO | WO 95/33059 | 12/1995 |
| WO | WO 96/23071 | 8/1996 |
| WO | WO 97/15663 | 1/1997 |
| WO | WO 97/07215 | 2/1997 |
| WO | WO 97/10354 | 3/1997 |
| WO | WO 97/12037 | 3/1997 |
| WO | WO 99/67290 | 12/1999 |
| WO | WO 00/34317 | 6/2000 |
| WO | WO 00/73451 | 12/2000 |
| WO | WO 00/75314 | 12/2000 |
| WO | WO 01/23556 | 4/2001 |
| WO | WO 01/85790 | 11/2001 |
| WO | WO 02/00721 | 1/2002 |
| WO | WO 02/29060 | 4/2002 |
| WO | WO 02/077230 | 10/2002 |
| WO | WO 03/060090 | 7/2003 |
| WO | WO 2003/072740 | 9/2003 |
| WO | WO 03/092602 | 11/2003 |
| WO | WO 2004/003140 | 1/2004 |
| WO | WO 2004/085476 | 10/2004 |
| WO | WO 2004/091543 | 10/2004 |
| WO | WO 2006/004663 | 1/2006 |
| WO | WO 2006/063864 | 6/2006 |
| WO | WO 2006/070286 | 7/2006 |
| WO | WO 2006/081573 | 8/2006 |
| WO | WO 2006/088855 | 8/2006 |
| WO | WO 2006/088955 | 8/2006 |
| WO | WO 2006/088956 | 8/2006 |
| WO | WO 2006/118959 | 11/2006 |
| WO | WO 2006/119062 | 11/2006 |
| WO | WO 2006/122079 | 11/2006 |
| WO | WO 2007/133816 | 11/2007 |
| WO | WO2007133816 A2 | 11/2007 |
| WO | WO 2007/142325 | 12/2007 |
| WO | WO 2008/103432 | 8/2008 |
| WO | WO 2008/132453 | 11/2008 |
| WO | WO 2009/041613 | 4/2009 |
| WO | WO 2009/041621 | 4/2009 |
| WO | WO 2009/041643 | 4/2009 |
| WO | WO 2009/072598 | 6/2009 |
| WO | WO 2009/072604 | 6/2009 |

OTHER PUBLICATIONS

USPTO Non-Final Office Action U.S. Appl. No. 12/205,799, mailed Feb. 8, 2010, 27 pages.

Fish & Richardson P.C. Reply to Restriction Requirement dated Oct. 9, 2009 in U.S. Appl. No. 12/205,753, filed Nov. 4, 2009, 1 page.

USPTO Non-Final Office Action in U.S. Appl. No. 12/325,556, mailed Jan. 28, 2010, 20 pages.

USPTO Non-Final Office Action in U.S. Appl. No. 12/325,591, mailed Dec. 7, 2009, 19 pages.

USPTO Non-Final Office Action in U.S. Appl. No. 12/325,617, mailed Dec. 7, 2009, 19 pages.

USPTO Non-Final Office Action in U.S. Appl. No. 12/325,631, mailed Dec. 24, 2009, 21 pages.

Castellani et al., Interleukin-31: A New Cytokine Involved in Inflammation of the Skin, Int. J. of Immunopathol. and Pharmacol., 19(1):1-4 (2006).

Diveau et al., "Predominant expression of the long isoform of the GP130-like (GPL) receptor is required for interleukin-31 signaling," Eur. Cytokine Netw., 15(4):291-302 (2004).

European Search Report for App. Ser. No. EP 07 74 4945, dated Oct. 29, 2009, 4 pages.

Bilsborough et al., "IL-31 is associated with cutaneous lymphocyte antigen-positive skin homing T cells in patients with atopic dermatitis," J. Allergy Clin. Immunol., 117:418-425 (2006).

Higa et al., "Administration of anti-interleukin 18 antibody fails to inhibit development of dermatitis in atopic dermatitis-model mice NC/Nga," Br. J. Dermatol., 149:39-45 (2003).

Sonkoly et al., "IL-31: A new link between T cells and pruritus in atopic skin inflammation," J. Allergy Clin. Immunol., 117:411-417 (2006).

International Bureau of WIPO, International Preliminary Report on Patentability for App. Ser. No. PCT/JP2007/061625, dated Jan. 13, 2009, 11 pages.

USPTO Final Office Action in U.S. Appl. No. 11/595,320, mailed Mar. 19, 2010, 26 pages.

USPTO Non-Final Office Action in U.S. Appl. No. 12/205,753, mailed Mar. 5, 2010, 24 pages.

Fish & Richardson P.C. Reply to Office Action dated Dec. 7, 2009 in U.S. Appl. No. 12/325,591, filed Jun. 4, 2010, 9 pages.

Fish & Richardson P.C. Reply to Office Action dated Dec. 7, 2009 in U.S. Appl. No. 12/325,617, filed Jun. 4, 2010, 8 pages.

Fish & Richardson P.C. Amendment in Reply to Action dated Feb. 8, 2010 in U.S. Appl. No. 12/205,799, filed Aug. 5, 2010, 6 pages.

Fish & Richardson P.C. Amendment in Reply to Action dated Jan. 28, 2010 in U.S. Appl. No. 12/325,556, filed Jul. 27, 2010, 4 pages.

Fish & Richardson P.C. Amendment in Reply to Action dated Dec. 24, 2009 in U.S. Appl. No. 12/325,631, filed Jun. 23, 2010, 10 pages.

USPTO Non-Final Office Action in U.S. Appl. No. 12/325,631, mailed Sep. 1, 2010, 9 pages.

U.S. Appl. No. 11/980,117, filed Oct. 30, 2007, Maeda et al.

U.S. Appl. No. 11/980,135, filed Oct. 30, 2007, Maeda et al.

U.S. Appl. No. 12/253,506, filed Oct. 17, 2008, Maeda et al.

Abbas et al., Cellular and Molecular Immunology, Second edition, W.B. Saunders Co., Philadelphia, pp. 47-48 (1994).

Alexander et al., "Suckling defect in mice lacking the soluble haemopoietin receptor NR6," Curr. Biol., 9:605-608 (1999).

Baumgartner et al., "The role of the WSXWS equivalent motif in growth hormone receptor function," J. Biol. Chem., 269:29094-29101 (1994).

Bepler et al., "A 1.4-Mb high-resolution physical map and contig of chromosome segment 11p15.5 and genes in LOH11A metastasis suppressor region," Genomics, 55:164-175 (1991).

Bork et al., "Go hunting in sequence databases but watch out for the traps," Trends Genet., 12:425-427 (1996).

Bork, "Powers and Pitfalls in Sequence Analysis: The 70% Hurdle," Genome Res., 10:398-400 (2000).

Cioffi et al., "Novel B219/OB receptor isoforms: Possible role of leptin in hematopoiesis and reproduction," Nat. Med., 2:585-589 (1996).

Cosman, "A new cytokine receptor superfamily," Trends Biochem. Sci., 15:265-270 (1990).

Cosman, "The Hematopoietin Receptor Superfamily," Cytokine, 5:95-106 (1993).

(56) References Cited

OTHER PUBLICATIONS

Dillon et al., "Interleukin 31, a cytokine produced by activated T cells, induces dermatitis in mice," *Nat. Immunol.*, 5:752-760 (2004).
Dillon et al., "Transgenic Mice Overexpressing a Novel Cytokine (IL-31) Develop a Severe Pruritic Skin Phenotype Resembling Atopic Dermatitis," *Eur. Cytokine Netw.*, 14(suppl. 3):81 (#223) (2003).
Diveu et al., "GPL, a novel cytokine receptor related to gp130 and leukemia inhibitory factor receptor," *J. Biol. Chem.*, 278(50):49850-49859 (2003).
Donaldson et al., "The murine IL-13 receptor α2: Molecular cloning, characterization, and comparison with murine IL-13 receptor α2," *J. Immunol.*, 161:2317-24 (1998).
EMBL Accession No. AI123586 dated Sep. 8, 1998.
EMBL Accession No. W16834 dated May 4, 1996.
Gainsford et al., "Leptin can induce proliferation, differentiation, and functional activation of hemopoietic cells," *Proc. Natl. Acad. Sci. USA*, 93:14564-14568 (1996).
Genbank Accession No. AAM44229 (hIL-23R), Oct. 19, 2004.
GenBank Accession No. AF102051, Jan. 28, 1999.
Genbank Accession No. AY499342, Jul. 10, 2004.
Genbank Accession No. NM_139017, Aug. 3, 2005.
Genbank Accession No. AQ022781, Jun. 16, 1998.
Ghilardi et al., "A novel type I cytokine receptor is expressed on monocytes, signals proliferation, and activates STAT-3 and STAT-5," *J. Biol. Chem.*, 27:16831-36 (2002).
Hibi et al., "Molecular cloning and expression of an IL-6 signal transducer, gp130," *Cell*, 63:1149-57 (1990).
Hilton et al., "Cloning and characterization of a binding subunit of the interleukin 13 receptor that is also a component of the interleukin 4 receptor," *Proc. Natl. Acad. Sci. USA*, 93:497-501 (1996).
Hilton et al., "Cloning of a murine IL-11 receptor α-chain; requirement for gp 130 for high affinity binding and signal transduction," *The EMBO Journal*, 13(20):4765-4775 (1994).
Irnaten et al., "Prediction of epitopes and production of monoclonal antibodies against gastric H,K-ATPase," *Protein Eng.*, 11:949-955 (1998).
Jabbour et al., "Expression of functional prolactin receptors in non-pregnant human endometrium: j anus kinase-2, signal transducer . . . ," *J. Clin. Endocrinol. Metab.*, 83:2545-53 (1998).
Kernebeck et al., "The signal transducer gp 130: solution structure of the carboxy-terminal domain of the cytokine receptor homology region," *Protein Sci.*, 8:5-12 (1999).
Mahairas et al., "Sequence-tagged connectors: A sequence approach to mapping and scanning the human genome," *Proc. Natl. Acad. Sci. USA*, 96:9730-44 (1999).
Matsuno et al., "Treatment of rheumatoid synovitis with anti-reshaping human interleukin-6 receptor monoclonal antibody," *Arthritis Rheumatism*, 41:2014-21 (1998).
Matthews et al., "A receptor tyrosine kinase specific to hematopoietic stem and progenitor cell-enriched populations," *Cell*, 65:1143-52 (1991).
Meinkoth and Wahl, "Hybridization of Nucleic Acids Immobilized on Solid Supports," *Anal. Biochem.*, 138:267-284 (1984).
Miyajima et al., "Cytokine receptors and signal transduction," *Annu. Rev. Immunol.*, 10:295-331, (1992).
Miyazaki et al., "The integrity of the conserved 'WS motif' common to IL-2 and other cytokine receptors is essential for ligand binding and signal transduction," *EMBO J.*, 10:3191-97 (1991).
Murakami et al., "Critical cytoplasmic region of the interleukin 6 signal transducer gp130 is conserved in the cytokine receptor family," *Proc. Natl. Acad. Sci.*, 88:11349-53 (1991).
Nagata et al., "Novel IL-31 cytokine," *Rheumatol.*, 35:282-286 (2006).
Nishimoto et al., "Improvement in Castleman's disease by humanized anti-interleukin-6 receptor antibody therapy," *Blood*, 95:56-61 (2001).
Nishimoto et al., "Toxicity, pharmacokinetics, and dose-finding study of repetitive treatment with the humanized anti-interleukin 6 receptor antibody MRA in rheumatoid arthritis. Phase I/II clinical study," *J. Rheumatol.*, 30:1426-35 (2003).
Oppmann et al., "Novel p19 protein engages IL-12p40 to form a cytokine, IL-23, with biological activities similar as well as distinct from IL-12," *Immunity*, 13:715-725 (2000).
Ozaki et al., "Cytokine receptor pleiotropy and redundancy," *J. Biol. Chem.*, 277:29355-56 (2002).
Parham, et al., "A receptor for the heterodimeric cytokine IL-23 is composed of IL-12Rβ1 and a novel cytokine receptor subunit, IL-23R," *J. Immunol.*, 168:5699-5708 (2002).
Robb et al., "Structural analysis of the gene encoding the murine interleukin-11 receptor α-chain and a related locus," *J. Biol. Chem.*, 271:13754-61 (1996).
Saito et al., "Molecular closing of a murine IL-6 receptor-associated signal transducer, gp130, and its regulated expression in vivo," *J. Immunol.*, 148:4066-71 (1992).
Sato et al., "Reshaping a human antibody to inhibit the interleukin 6-dependent tumor cell growth," *Cancer Res.*, 53:851-856 (1993).
Simard et al., "Ontogeny of Growth hormone receptors in human tissues: an immunohistochemical study," *J. Clin. Endocrinol. Metab.*, 81:3097-3102 (1996).
Wells et al., "Hematopoietic receptor complexes," *Annu. Rev. Biochem.*, 65:609-634 (1996).
Wells, "Additivity of Mutational Effects in Proteins," *Biochem.*, 29:8509-17 (1990).
USPTO Restriction Requirement in U.S. Appl. No. 10/105,930, mailed May 22, 2003, 6 pages.
Fish & Richardson P.C. Response to Restriction Requirement dated May 22, 2003 in U.S. Appl. No. 10/105,930, filed Jun. 17, 2003, 1 page.
USPTO Non-Final Office Action in U.S. Appl. No. 10/105,930, mailed Sep. 29, 2003, 19 pages.
Fish & Richardson P.C Amendment in Reply to Action dated Sep. 29, 2003 in U.S. Appl. No. 10/105,930, filed Mar. 26, 2004, 31 pages.
USPTO Final Office Action in U.S. Appl. No. 10/105,930, mailed Jun. 28, 2004, 16 pages.
Fish & Richardson P.C Amendment in Reply to Action dated Jun. 28, 2004 in U.S. Appl. No. 10/105,930, filed Nov. 23, 2004, 34 pages.
USPTO Advisory Action in U.S. Appl. No. 10/105,930, mailed Feb. 4, 2005, 4 pages.
Fish & Richardson P.C Appeal Brief in U.S. Appl. No. 10/105,930, filed Jun. 20, 2005, 27 pages.
USPTO Notice of Allowance in U.S. Appl. No. 10/105,930, mailed Sep. 14, 2005, 6 pages.
Japanese Patent Office, International Search Report for U.S. Appl. No. PCT/JP00/06654, mailed Dec. 26, 2000, 4 pages.
USPTO Non-Final Office Action in U.S. Appl. No. 11/274,375, mailed May 12, 2006, 17 pages.
USPTO Non-Final Office Action in U.S. Appl. No. 11/595,320, mailed Aug. 14, 2007, 14 pages.
Fish & Richardson P.C Amendment in Reply to Action dated Aug. 14, 2007 in U.S. Appl. No. 11/595,320, filed Feb. 14, 2008, 23 pages.
USPTO Non-Final Office Action in U.S. Appl. No. 11/595,320, mailed May 28, 2008, 13 pages.
Fish & Richardson P.C Amendment in Reply to Action dated May 28, 2008 in U.S. Appl. No. 11/595,320, filed Nov. 26, 2008, 6 pages.
USPTO Final Office Action in U.S. Appl. No. 11/595,320, mailed Feb. 26, 2009, 10 pages.
Fish & Richardson P.C Amendment in Reply to Action dated Feb. 26, 2009 in U.S. Appl. No. 11/595,320, filed Apr. 24, 2009, 3 pages.
USPTO Non-Final Office Action in U.S. Appl. No. 11/595,320, mailed Jun. 4, 2009, 10 pages.
USPTO Restriction Requirement in U.S. Appl. No. 10/006,265, mailed Dec. 13, 2004, 10 pages.
Fish & Richardson P.C. Response to Restriction Requirement dated Dec. 13, 2004 in U.S. Appl. No. 10/006,265, filed Jan. 10, 2005, 1 page.
USPTO Non-Final Office Action in U.S. Appl. No. 10/006,265, mailed Mar. 14, 2005, 8 pages.
Fish & Richardson P.C. Amendment in Reply to Action dated Mar. 14, 2005 in U.S. Appl. No. 10/006,265, filed Sep. 14, 2005, 33 pages.
USPTO Final Office Action in U.S. Appl. No. 10/006,265, mailed Dec. 21, 2005, 12 pages.

(56) References Cited

OTHER PUBLICATIONS

USPTO Non-Final Office Action in U.S. Appl. No. 10/006,265, mailed Jul. 26, 2006, 13 pages.
Fish & Richardson P.C. Amendment in Reply to Action dated Jul. 26, 2006 in U.S. Appl. No. 10/006,265, filed Jan. 5, 2007, 22 pages.
USPTO Final Office Action in U.S. Appl. No. 10/006,265, mailed Mar. 22, 2007, 9 pages.
Fish & Richardson P.C. Amendment in Reply to Action dated Mar. 22, 2007 in U.S. Appl. No. 10/006,265, filed Jun. 22, 2007, 7 pages.
USPTO Advisory Action in U.S. Appl. No. 10/006,265, mailed Jul. 30, 2007, 7 pages.
USPTO Non-Final Action in U.S. Appl. No. 10/006,265, mailed Oct. 30, 2007, 8 pages.
Fish & Richardson P.C. Amendment in Reply to Action dated Oct. 30, 2007 in U.S. Appl. No. 10/006,265, filed Jan. 30, 2008, 6 pages.
USPTO Notice of Allowance in U.S. Appl. No. 10/006,265, mailed Apr. 11, 2008, 15 pages.
Fish & Richardson P.C. Response to Notice of Allowance dated Apr. 11, 2008 in U.S. Appl. No. 10/006,265, filed Jul. 10, 2008, 6 pages.
Japanese Patent Office, International Search Report for App. Ser. No. PCT/JP00/03556, mailed Sep. 5, 2000, 1 page.
Japanese Patent Office, International Preliminary Report on Patentability for App. Ser. No. PCT/JP00/03556, dated May 21, 2001, 3 pages.
European Search Report for App. Ser. No. EP 00 93 1646, dated Dec. 30, 2004, 4 pages.
Japanese Patent Office, International Search Report for App. Ser. No. PCT/JP2007/061625, mailed Sep. 18, 2007, 2 pages.
USPTO Restriction Requirement in U.S. Appl. No. 12/325,556, mailed Aug. 25, 2009, 7 pages.
Fish & Richardson P.C. Reply to Restriction Requirement dated Aug. 25, 2009 in U.S. Appl. No. 12/325,556, filed Sep. 21, 2009, 1 page.
USPTO Restriction Requirement in U.S. Appl. No. 12/325,591, mailed Aug. 25, 2009, 7 pages.
Fish & Richardson P.C. Reply to Restriction Requirement dated Aug. 25, 2009 in U.S. Appl. No. 12/325,591, filed Sep. 21, 2009, 1 page.
USPTO Restriction Requirement in U.S. Appl. No. 12/325,631, mailed Aug. 25, 2009, 7 pages.
Fish & Richardson P.C. Reply to Restriction Requirement dated Aug. 25, 2009 in U.S. Appl. No. 12/325,631, filed Sep. 21, 2009, 1 page.
USPTO Restriction Requirement in U.S. Appl. No. 12/325,617, mailed Aug. 26, 2009, 7 pages.
Fish & Richardson P.C. Reply to Restriction Requirement dated Aug. 26, 2009 in U.S. Appl. No. 12/325,617, filed Sep. 21, 2009, 1 page.
USPTO Restriction Requirement in U.S. Appl. No. 12/205,799, mailed Oct. 9, 2009, 7 pages.
USPTO Restriction Requirement in U.S. Appl. No. 12/205,753, mailed Oct. 9, 2009, 7 pages.
Bilsborough, "IL-31 is associated with cutaneous lymphocyte antigen-positive skin homing T cells in patients with atopic dermatitis," J. Allergy Clin. Immunol., 117(2):418-25 (2006).
International Search Report for App. Ser. No. PCT/JP2008/072142, mailed Jan. 6, 2009, 2 pages.
International Preliminary Report on Patentability for App. Ser. No. PCT/JP2008/072142, dated Aug. 10, 2010, 5 pages.
MacNeal, Robert J., "Itching (Pruritus)," Merck Manual, May 2009 [retrieved on Jun. 10, 2011]. Retrieved from the Internet: http://www.merckmanuals.com/professional/sec10/ch109/ch109d.html, 6 pages.
Zhang et al., "Structures and biological functions of IL-31 and IL-31 receptors," *Cytokine Growth Factor Rev.*, 19:347-356 (2008).
USPTO Non-Final Office Action in U.S. Appl. No. 12/746,229, mailed Jun. 16, 2011, 16 pages.
Cork et al., "Epidermal barrier dysfunction in atopic dermatitis," *J. Invest. Dermatol.*, 129(8):1892-908 (2009).
Levin et al., "Optimizing the affinity and specificity of proteins with molecular display," *Mol. Biosyst.*, 2(1):49-57 (2006) (Epub Nov. 8, 2005).

Onda et al., "Lowering the isoelectric point of the Fv portion of recombinant immunotoxins leads to decreased nonspecific animal toxicity without affecting antitumor activity," *Cancer Res.*, 61(13):5070-5077 (2001).
Chirino et al., "Minimizing the immunogenicity of protein therapeutics," *Drug Discov. Today*, 9(2):82-90 (2004).
Ewert et al., "Stability improvement of antibodies for extracellular and intracellular applications: CDR grafting to stable frameworks and structure-based framework engineering," *Methods*, 34:184-199 (2004).
Grimstad et al., "Anti-interleukin-31-antibodies ameliorate scratching behaviour in NC/Nga mice: a model of atopic dermatitis," *Exp. Dermatol.*, 18(1):35-43 (2009).
Hanes et al., "Picomolar affinity antibodies from a fully synthetic naive library selected and evolved by ribosome display," *Nat. Biotechnol.*, 18(12):1287-1292 (2000).
Neis et al., "Enhanced expression levels of IL-31 correlate with IL-4 and IL-13 in atopic and allergic contact dermatitis," *J. Allergy Clin. Immunol.*, 118(4):930-937 (2006).
Raap et al., "Correlation of IL-31 serum levels with severity of atopic dermatitis," *J. Allergy Clin. Immunol.*, 122(2):421-423 (2008).
Tan et al., "Engineering the isoelectric point of a renal cell carcinoma targeting antibody greatly enhances scFv solubility," *Immunotechnology*, 4(2):107-114 (1998).
Vagi et al., "Interleukin-31 stimulates production of inflammatory mediators from human colonic subepithelial myofibroblasts," *Int. J. Mol. Med.*, 19(6):941-946 (2007).
European Search Report for App. Ser. No. EP 11 169 972, dated Aug. 29, 2011, 11 pages.
Fish & Richardson P.C. Amendment in Reply to Non-Final Office Action dated Jun. 16, 2011 in U.S. Appl. No. 12/746,229, filed Dec. 13, 2011, 7 pages.
International Preliminary Report on Patentability for App. Ser. No. PCT/JP2009/070376, dated Jul. 5, 2011, 11 pages.
USPTO Restriction Requirement in U.S. Appl. No. 12/746,229, dated Apr. 12, 2012, 5 pages.
R&D Systems (R&D Systems, Anti-human IL-31 RA Antibody, Catalog #AF2769, Oct. 2008).
Fish & Richardson P.C. Amendment and Response to Restriction Requirement dated Apr. 12, 2012 in U.S. Appl. No. 12/746,229, filed May 10, 2012, 7 pages.
USPTO Restriction Requirement in U.S. Appl. No. 12/746,229, dated Jun. 25, 2012, 4 pages.
Fish & Richardson P.C. Response to Restriction Requirement dated Jun. 25, 2012 in U.S. Appl. No. 12/746,229, filed Jul. 24, 2012, 2 pages.
USPTO Restriction Requirement in U.S. Appl. No. 12/745,781, dated Jul. 30, 2012, 9 pages.
Pakula et al., "Genetic Analysis of Protein Stability and Function," *Annu. Rev. Genet.*, 23:289-310 (1989).
Roitt et al., Immunology, M., Mir, (2000), pp. 110-111 (in Russian, with what is believed to be a published English equivalent of those pages taken from Roitt et al., "Antibody Structure and Function," Immunology, Fifth Ed., (1998), pp. 80-81).
USPTO Notice of Allowance in U.S. Appl. No. 12/746,229, dated Mar. 27, 2013, 8 pages.
Fish & Richardson P.C., Amendment in Reply to Office Action dated Oct. 18, 2012 in U.S. Appl. No. 12/745,781, filed on Apr. 17, 2013, 23 pages.
Fish & Richardson P.C., Response to Restriction Requirement dated Dec. 13, 2012 in U.S. Appl. No. 12/809,138, filed on Apr. 5, 2013, 2 pages.
Rose-John et al., "Interleukin-6 biology is coordinated by membrane-bound and soluble receptors: role in inflammation and cancer," *J. Leukoc. Biol.*, 80(2):227-36 (2006).
USPTO Final Office Action in U.S. Appl. No. 12/745,781, dated May 21, 2013, 16 pages.
Burgess et al., "Possible dissociation of the heparin-binding and mitogenic activities of heparin-binding (acidic fibroblast) growth factor-1 from its receptor-binding activities by site-directed mutagenesis of a single lysine residue," *J. Cell. Biol.*, 111:2129-2138 (1990).

(56) References Cited

OTHER PUBLICATIONS

Lazar et al., "Transforming growth factor alpha: mutation of aspartic acid 47 and leucine 48 results in different biological activities," *Mol. Cell. Biol.*, 8:1247-1252 (1988).

Padlan et al., "Identification of specificity-determining residues in antibodies," *FASEB J.*, 9:133-139 (1995).

R&D Systems (R&D Systems, Biotinylated Anti-human IL-31 RA Antibody, Catalog #BAF2769, Nov. 2005), 1 page.

USPTO Notice of Allowance in U.S. Appl. No. 12/746,229, dated Aug. 23, 2012, 9 pages.

USPTO Restriction Requirement in U.S. Appl. No. 12/745,781, dated Sep. 4, 2012, 10 pages.

Fish & Richardson P.C., Response to Restriction Requirement dated Sep. 4, 2012 in U.S. Appl. No. 12/745,781, filed Sep. 21, 2012, 176 pages.

USPTO Non-Final Office Action in U.S. Appl. No. 12/745,781, dated Oct. 18, 2012, 21 pages.

U.S. Appl. No. 14/047,316, filed Oct. 7, 2013, Kuramochi et al.

USPTO Notice of Allowance in U.S. Appl. No. 12/746,229, dated Feb. 12, 2013, 7 pages.

Krauss et al., "Impact of antibody framework residue VH-71 on the stability of a humanised anti-MUC1 scFv and derived immunoenzyme," *Br. J. Cancer*, 90:1863-70 (2004).

Marks et al., "By-passing immunization: building high affinity human antibodies by chain shuffling," *Biotechnology (N.Y.)*, 10(7):779-83 (1992).

Ohno et al., "Antigen-binding specificities of antibodies are primarily determined by seven residues of VH," *Proc. Natl. Acad. Sci. U.S.A.*, 82(9):2945-9 (1985).

Roitt et al., *Immunology*, M., Mir, 110, 150, 537-9 (2000) (with English translations).

Rudikoff et al., "Single amino acid substitution altering antigen-binding specificity," *Proc. Natl. Acad. Sci. U.S.A.*, 79(6):1979-83 (1982).

Singer et al., Genes & Genomes (Russian translation from English) 1:63 (1998) (with English translation).

Yang et al., "CDR walking mutagenesis for the affinity maturation of a potent human anti-HIV-1 antibody into the picomolar range," *J Mol. Biol.*, 254(3):392-403 (1995).

USPTO Notice of Allowance in U.S. Appl. No. 12/746,229, dated Dec. 17, 2012, 7 pages.

USPTO Restriction Requirement in U.S. Appl. No. 12/809,138, dated Dec. 13, 2012, 8 pages.

\* cited by examiner

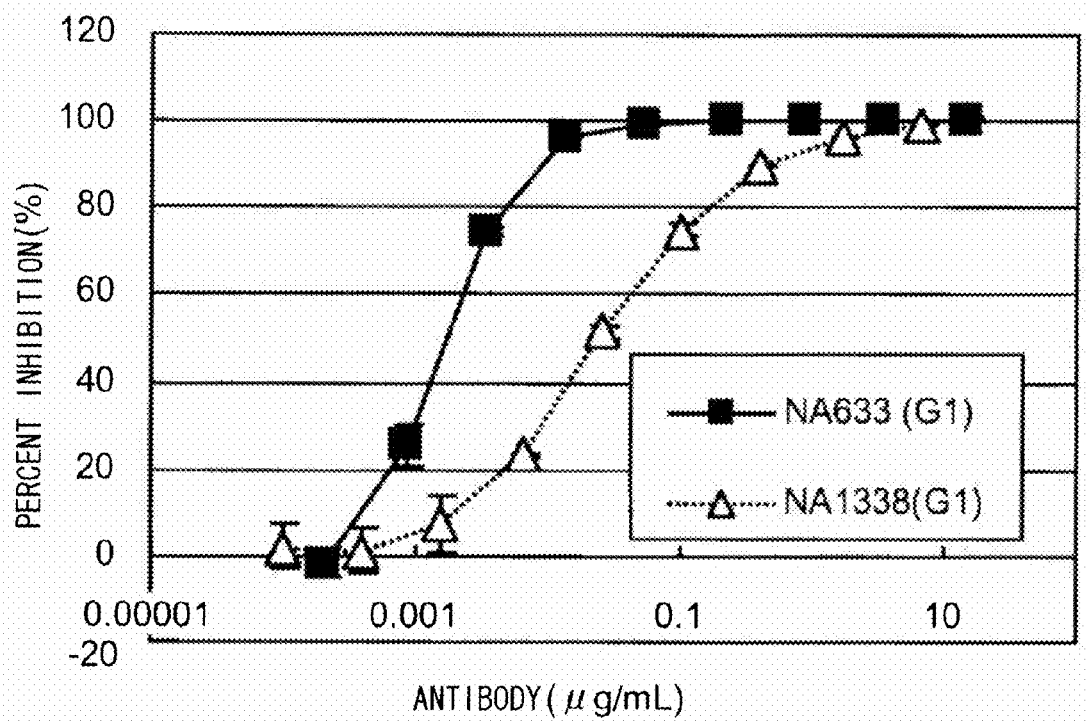

| | |
|---|---|
| CYNOMOL | MMMTWALWMFPLLCKFGLAALPAKPENISCVYYYRKNLTCTWSPGKETSYTQYTAKRTYAFGKKHDNCTTSSSTSENRASCSFFLPRITIPDNYTIEVEA |
| HUMAN | MMMTWALWML PSLCKFSLAALPAKPENISCVYYYYRKNLTCTWSPGKETSYTQYTVKRTYAFGEKHDNCTTNSSTSENRASCSFFLPRITIPDNYTIEVEA |
| | |
| CYNOMOL | ENGDGVIKSDMTCWRLEDIAKTEPPEIFSVKPVLGIKRMIREWIKPELAPVSSDLKYALRFRTVNSTSWMEVNFAKNRKDTNQTYNLMGLQAFTEYVVA |
| HUMAN | ENGDGVIKSHMTYWRLENIAKTEPPKIFRVKPVLGIKRMIQIEWIKPELAPVSSDLKYTLRFRTVNSTSWMEVNFAKNRKDKNQTYNLTGLQPFTEYVIA |
| | |
| CYNOMOL | LRCAVKESKFWSDWSQEKMGMTEEEAPCGLELWRVLKPTEVDGRRPVRLLWKKARGAPVLEKTLGYNIWYFPENNTNLTETVNTTNQQLELHLGGESYWV |
| HUMAN | LRCAVKESKFWSDWSQEKMGMTEEEAPCGLELWRVLKPAEADGRRPVRLLWKKARGAPVLEKTLGYNIWYYPESNTNLTETMNTTNQQLELHLGGESFWV |
| | |
| CYNOMOL | SMISYNSLGKSPVTTLRIPAIQEKSFRCIEVMQACLAEDQLVVKWQSSALDVNTWMIEWFPDMDSEHPTLSWESVSQATNWTIQQDKLKPFWCYNISVYP |
| HUMAN | SMISYNSLGKSPVATLRIPAIQEKSFQCIEVMQACVAEDQLVVKWQSSALDVNTWMIEWFPDVDSEPTTLSWESVSQATNWTIQQDKLKPFWCYNISVYP |
| | |
| CYNOMOL | MLHDKVGEPYSIQAYAKEGIPSKGPETKVENIGVKTVTITWKEIPKSERKGIICNYTIFYQAEGGKGFSKTVNSSILQYGLESLKRKTSYTVRVWASTSA |
| HUMAN | MLHDKVGEPYSIQAYAKEGVPSEGPETKVENIGVKTVTITWKEIPKSERKGIICNYTIFYQAEGGKGFSKTVNSSILQYGLESLKRKTSYIVQVWASTSA |
| | |
| CYNOMOL | GGINGTSINFKTLSFSVFEIILITSLIGGGLLILILIILTVAYGLKKPNKLTHLCWPSVPNPAESSIATWRGDDFKDKLNLKESDDSVNTEDRILKPCSTPS |
| HUMAN | GGTNGTSINFKTLSFSVFEIILITSLIGGGLLILILIILTVAYGLKKPNKLTHLCWPTVPNPAESSIATWHGDDFKDKLNLKESDDSVNTEDRILKPCSTPS |
| | |
| CYNOMOL | DKLVIDKSVVNFGNVLQEMFTDEARTGQENNLGGEKNEYVTHPFRADCPLGKSFEELPVSPEIPPRKSQYLRSRMPEGTCLEAEEQLLVSGQSLESLAPD |
| HUMAN | DKLVIDKLVVNFGNVLQEIFTDEARTGQENNLGGEKNGYVTCPFRPDCPLGKSFEELPVSPEIPPRKSQYLRSRMPEGTRPEAKEQLLFSGQSL——VPD |
| | |
| CYNOMOL | HVREAAAPNPYLKNSVTTREFLVSQKLPEHTKGEV 735 (SEQ ID NO: 24) |
| HUMAN | HLCEEGAPNPYLKNSVTAREFLVSEKLPEHTKGEV 732 (SEQ ID NO: 7) |

FIG. 10

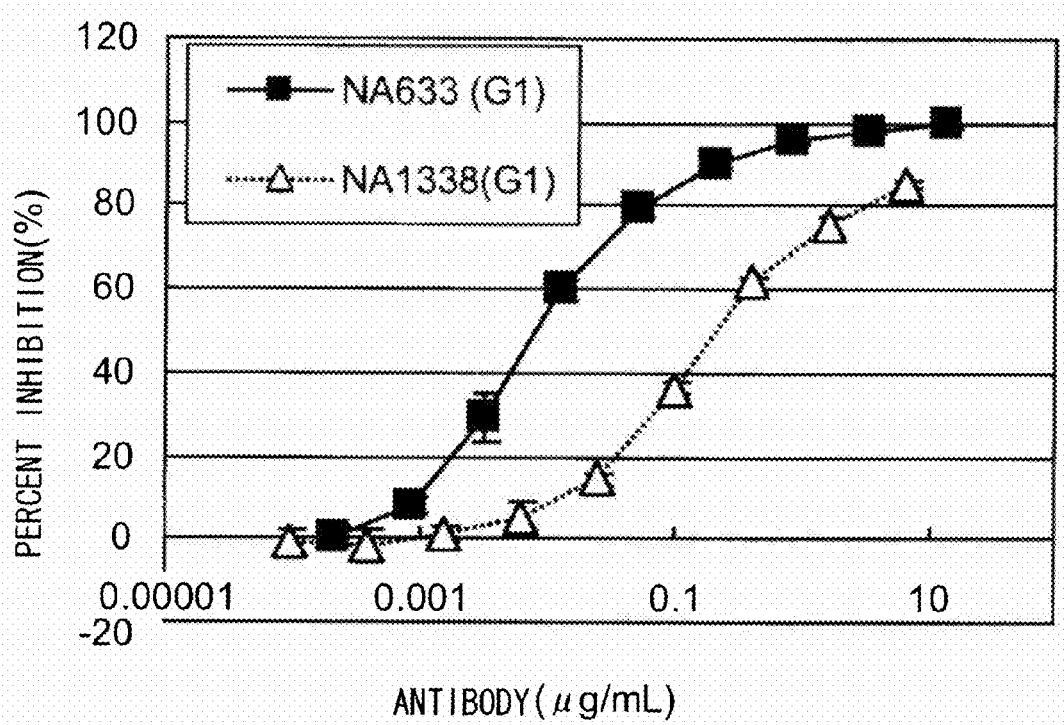

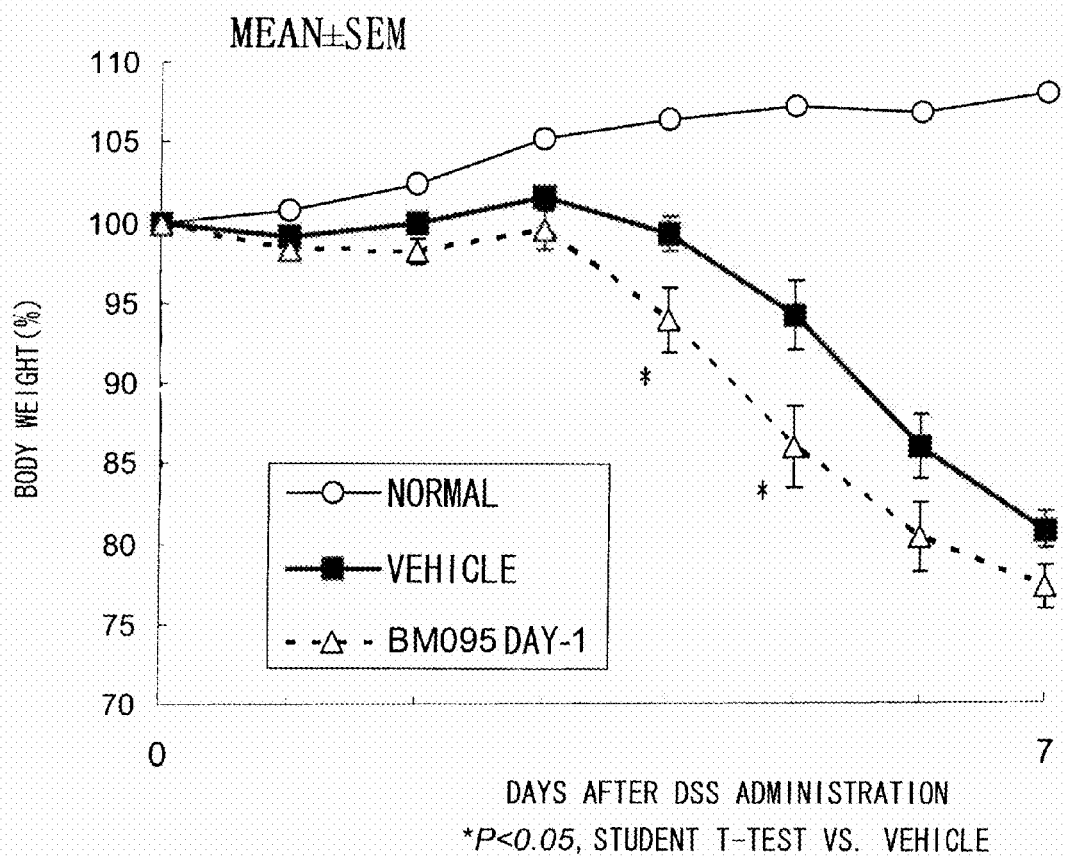

SEQUENCE LISTING

```
<160> NUMBER OF SEQ ID NOS: 24

<210> SEQ ID NO 1
<211> LENGTH: 125
<212> TYPE: PRT
<213> ORGANISM: Homo sapiens

<400> SEQUENCE: 1

Gln Val Gln Leu Val Gln Ser Gly Ala Glu Val Lys Lys Pro Gly Ala
```

```
1               5                   10                  15
Ser Val Lys Val Ser Cys Lys Ala Ser Gly Tyr Thr Phe Thr Gly Tyr
                    20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Asp Val Val Pro Ala Ala Met Ser Phe Tyr Tyr Gly Met
                    100                 105                 110

Asp Val Trp Gly Arg Gly Thr Leu Val Thr Val Ser Ser
            115                 120                 125

<210> SEQ ID NO 2
<211> LENGTH: 375
<212> TYPE: DNA
<213> ORGANISM: Homo sapiens

<400> SEQUENCE: 2
caggtccagc tggtacagtc tggggctgag gtgaagaagc ctggggcctc agtgaaggtc     60
tcctgcaagg cttctggata caccttcacc ggctactata tgcactgggt gcgacaggcc    120
cctggacaag gcttgagtg gatgggatgg atcaaccct a acagtggtgg cacaaactat    180
gcacagaagt tcagggcag ggtcaccatg accagggaca cgtccatcag cacagcctac    240
atggagctga gcaggctgag atctgacgac acggccgtgt attactgtgc gagagaggac    300
gtagtaccag ctgctatgtc attctactac ggtatggacg tctggggccg aggaaccctg    360
gtcaccgtct cgagt                                                      375

<210> SEQ ID NO 3
<211> LENGTH: 109
<212> TYPE: PRT
<213> ORGANISM: Homo sapiens

<400> SEQUENCE: 3

Leu Pro Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Thr Val
                    20                  25                  30

Tyr Trp Tyr Gln Gln Glu Pro Gly Gln Ala Pro Val Leu Val Val Tyr
            35                  40                  45

Asp Asp Thr Asp Arg Pro Ala Gly Ile Pro Glu Arg Phe Ser Gly Ala
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Thr Asp His
                85                  90                  95

Gly Val Phe Gly Gly Gly Thr Lys Leu Thr Val Leu Gly
            100                 105

<210> SEQ ID NO 4
<211> LENGTH: 327
<212> TYPE: DNA
<213> ORGANISM: Homo sapiens
```

<400> SEQUENCE: 4

```
ctgcctgtgc tgactcagcc cccctcggtg tcagtggccc caggacagac ggccaggatt        60
acctgtgggg gaaacaacat tggaagtaaa actgtgtact ggtaccagca ggagccaggc       120
caggcccctg tgttggtcgt ctatgatgat accgaccggc ccgcaggaat ccctgagcgc       180
ttctctggcg ccaactctgg gaacacggcc accctgacca tcagcagggt cgaagccggg       240
gatgaggccg actattactg tcaggtgtgg gatagtagta ctgatcatgg ggttttcggc       300
ggagggacca agctgaccgt cctaggt                                           327
```

<210> SEQ ID NO 5
<211> LENGTH: 716
<212> TYPE: PRT
<213> ORGANISM: Mus musculus

<400> SEQUENCE: 5

```
Met Trp Thr Leu Ala Leu Trp Ala Phe Ser Phe Leu Cys Lys Phe Ser
 1               5                   10                  15

Leu Ala Val Leu Pro Thr Lys Pro Glu Asn Ile Ser Cys Val Phe Tyr
            20                  25                  30

Phe Asp Arg Asn Leu Thr Cys Thr Trp Arg Pro Glu Lys Glu Thr Asn
        35                  40                  45

Asp Thr Ser Tyr Ile Val Thr Leu Thr Tyr Ser Tyr Gly Lys Ser Asn
    50                  55                  60

Tyr Ser Asp Asn Ala Thr Glu Ala Ser Tyr Ser Phe Pro Arg Ser Cys
65                  70                  75                  80

Ala Met Pro Pro Asp Ile Cys Ser Val Glu Val Gln Ala Gln Asn Gly
                85                  90                  95

Asp Gly Lys Val Lys Ser Asp Ile Thr Tyr Trp His Leu Ile Ser Ile
            100                 105                 110

Ala Lys Thr Glu Pro Pro Ile Ile Leu Ser Val Asn Pro Ile Cys Asn
        115                 120                 125

Arg Met Phe Gln Ile Gln Trp Lys Pro Arg Glu Lys Thr Arg Gly Phe
    130                 135                 140

Pro Leu Val Cys Met Leu Arg Phe Arg Thr Val Asn Ser Ser Arg Trp
145                 150                 155                 160

Thr Glu Val Asn Phe Glu Asn Cys Lys Gln Val Cys Asn Leu Thr Gly
                165                 170                 175

Leu Gln Ala Phe Thr Glu Tyr Val Leu Ala Leu Arg Phe Arg Phe Asn
            180                 185                 190

Asp Ser Arg Tyr Trp Ser Lys Trp Ser Lys Glu Glu Thr Arg Val Thr
        195                 200                 205

Met Glu Glu Val Pro His Val Leu Asp Leu Trp Arg Ile Leu Glu Pro
    210                 215                 220

Ala Asp Met Asn Gly Asp Arg Lys Val Arg Leu Leu Trp Lys Lys Ala
225                 230                 235                 240

Arg Gly Ala Pro Val Leu Glu Lys Thr Phe Gly Tyr His Ile Gln Tyr
                245                 250                 255

Phe Ala Glu Asn Ser Thr Asn Leu Thr Glu Ile Asn Asn Ile Thr Thr
            260                 265                 270

Gln Gln Tyr Glu Leu Leu Leu Met Ser Gln Ala His Ser Val Ser Val
        275                 280                 285

Thr Ser Phe Asn Ser Leu Gly Lys Ser Gln Glu Ala Ile Leu Arg Ile
    290                 295                 300
```

```
Pro Asp Val His Glu Lys Thr Phe Gln Tyr Ile Lys Ser Met Lys Ala
305                 310                 315                 320

Tyr Ile Ala Glu Pro Leu Leu Val Val Asn Trp Gln Ser Ser Ile Pro
            325                 330                 335

Ala Val Asp Thr Trp Ile Val Glu Trp Leu Pro Glu Ala Ala Met Ser
        340                 345                 350

Lys Phe Pro Ala Leu Ser Trp Glu Ser Val Ser Gln Val Thr Asn Trp
    355                 360                 365

Thr Ile Glu Gln Asp Lys Leu Lys Pro Phe Thr Cys Tyr Asn Ile Ser
370                 375                 380

Val Tyr Pro Val Leu Gly His Arg Val Gly Pro Tyr Ser Ile Gln
385                 390                 395                 400

Ala Tyr Ala Lys Glu Gly Thr Pro Leu Lys Gly Pro Glu Thr Arg Val
            405                 410                 415

Glu Asn Ile Gly Leu Arg Thr Ala Thr Ile Thr Trp Lys Glu Ile Pro
        420                 425                 430

Lys Ser Ala Arg Asn Gly Phe Ile Asn Asn Tyr Thr Val Phe Tyr Gln
    435                 440                 445

Ala Glu Gly Gly Lys Glu Leu Ser Lys Thr Val Asn Ser His Ala Leu
450                 455                 460

Gln Cys Asp Leu Glu Ser Leu Thr Arg Arg Thr Ser Tyr Thr Val Trp
465                 470                 475                 480

Val Met Ala Ser Thr Arg Ala Gly Gly Thr Asn Gly Val Arg Ile Asn
            485                 490                 495

Phe Lys Thr Leu Ser Ile Ser Val Phe Glu Ile Val Leu Leu Thr Ser
        500                 505                 510

Leu Val Gly Gly Gly Leu Leu Leu Ser Ile Lys Thr Val Thr Phe
    515                 520                 525

Gly Leu Arg Lys Pro Asn Arg Leu Thr Pro Leu Cys Cys Pro Asp Val
530                 535                 540

Pro Asn Pro Ala Glu Ser Ser Leu Ala Thr Trp Leu Gly Asp Gly Phe
545                 550                 555                 560

Lys Lys Ser Asn Met Lys Glu Thr Gly Asn Ser Gly Asp Thr Glu Asp
            565                 570                 575

Val Val Leu Lys Pro Cys Pro Val Pro Ala Asp Leu Ile Asp Lys Leu
        580                 585                 590

Val Val Asn Phe Glu Asn Phe Leu Glu Val Val Leu Thr Glu Glu Ala
    595                 600                 605

Gly Lys Gly Gln Ala Ser Ile Leu Gly Gly Glu Ala Asn Glu Tyr Val
610                 615                 620

Thr Ser Pro Ser Arg Pro Asp Gly Pro Pro Gly Lys Ser Phe Lys Glu
625                 630                 635                 640

Pro Ser Val Leu Thr Glu Val Ala Ser Glu Asp Ser His Ser Thr Cys
            645                 650                 655

Ser Arg Met Ala Asp Glu Ala Tyr Ser Glu Leu Ala Arg Gln Pro Ser
        660                 665                 670

Ser Ser Cys Gln Ser Pro Gly Leu Ser Pro Arg Glu Asp Gln Ala
    675                 680                 685

Gln Asn Pro Tyr Leu Lys Asn Ser Val Thr Thr Arg Glu Phe Leu Val
690                 695                 700

His Glu Asn Ile Pro Glu His Ser Lys Gly Glu Val
705                 710                 715
```

<210> SEQ ID NO 6
<211> LENGTH: 662
<212> TYPE: PRT
<213> ORGANISM: Homo sapiens

<400> SEQUENCE: 6

```
Met Lys Leu Ser Pro Gln Pro Ser Cys Val Asn Leu Gly Met Met Trp
1               5                   10                  15

Thr Trp Ala Leu Trp Met Leu Pro Ser Leu Cys Lys Phe Ser Leu Ala
            20                  25                  30

Ala Leu Pro Ala Lys Pro Glu Asn Ile Ser Cys Val Tyr Tyr Tyr Arg
        35                  40                  45

Lys Asn Leu Thr Cys Thr Trp Ser Pro Gly Lys Glu Thr Ser Tyr Thr
    50                  55                  60

Gln Tyr Thr Val Lys Arg Thr Tyr Ala Phe Gly Glu Lys His Asp Asn
65                  70                  75                  80

Cys Thr Thr Asn Ser Ser Thr Ser Glu Asn Arg Ala Ser Cys Ser Phe
                85                  90                  95

Phe Leu Pro Arg Ile Thr Ile Pro Asp Asn Tyr Thr Ile Glu Val Glu
            100                 105                 110

Ala Glu Asn Gly Asp Gly Val Ile Lys Ser His Met Thr Tyr Trp Arg
        115                 120                 125

Leu Glu Asn Ile Ala Lys Thr Glu Pro Pro Lys Ile Phe Arg Val Lys
    130                 135                 140

Pro Val Leu Gly Ile Lys Arg Met Ile Gln Ile Glu Trp Ile Lys Pro
145                 150                 155                 160

Glu Leu Ala Pro Val Ser Ser Asp Leu Lys Tyr Thr Leu Arg Phe Arg
                165                 170                 175

Thr Val Asn Ser Thr Ser Trp Met Glu Val Asn Phe Ala Lys Asn Arg
            180                 185                 190

Lys Asp Lys Asn Gln Thr Tyr Asn Leu Thr Gly Leu Gln Pro Phe Thr
        195                 200                 205

Glu Tyr Val Ile Ala Leu Arg Cys Ala Val Lys Glu Ser Lys Phe Trp
    210                 215                 220

Ser Asp Trp Ser Gln Glu Lys Met Gly Met Thr Glu Glu Glu Ala Pro
225                 230                 235                 240

Cys Gly Leu Glu Leu Trp Arg Val Leu Lys Pro Ala Glu Ala Asp Gly
                245                 250                 255

Arg Arg Pro Val Arg Leu Leu Trp Lys Lys Ala Arg Gly Ala Pro Val
            260                 265                 270

Leu Glu Lys Thr Leu Gly Tyr Asn Ile Trp Tyr Tyr Pro Glu Ser Asn
        275                 280                 285

Thr Asn Leu Thr Glu Thr Met Asn Thr Thr Asn Gln Gln Leu Glu Leu
    290                 295                 300

His Leu Gly Gly Glu Ser Phe Trp Val Ser Met Ile Ser Tyr Asn Ser
305                 310                 315                 320

Leu Gly Lys Ser Pro Val Ala Thr Leu Arg Ile Pro Ala Ile Gln Glu
                325                 330                 335

Lys Ser Phe Gln Cys Ile Glu Val Met Gln Ala Cys Val Ala Glu Asp
            340                 345                 350

Gln Leu Val Val Lys Trp Gln Ser Ser Ala Leu Asp Val Asn Thr Trp
        355                 360                 365

Met Ile Glu Trp Phe Pro Asp Val Asp Ser Glu Pro Thr Thr Leu Ser
    370                 375                 380
```

```
Trp Glu Ser Val Ser Gln Ala Thr Asn Trp Thr Ile Gln Gln Asp Lys
385                 390                 395                 400

Leu Lys Pro Phe Trp Cys Tyr Asn Ile Ser Val Tyr Pro Met Leu His
            405                 410                 415

Asp Lys Val Gly Glu Pro Tyr Ser Ile Gln Ala Tyr Ala Lys Glu Gly
        420                 425                 430

Val Pro Ser Glu Gly Pro Glu Thr Lys Val Glu Asn Ile Gly Val Lys
            435                 440                 445

Thr Val Thr Ile Thr Trp Lys Glu Ile Pro Lys Ser Glu Arg Lys Gly
        450                 455                 460

Ile Ile Cys Asn Tyr Thr Ile Phe Tyr Gln Ala Glu Gly Gly Lys Gly
465                 470                 475                 480

Phe Ser Lys Thr Val Asn Ser Ser Ile Leu Gln Tyr Gly Leu Glu Ser
            485                 490                 495

Leu Lys Arg Lys Thr Ser Tyr Ile Val Gln Val Met Ala Ser Thr Ser
            500                 505                 510

Ala Gly Gly Thr Asn Gly Thr Ser Ile Asn Phe Lys Thr Leu Ser Phe
        515                 520                 525

Ser Val Phe Glu Ile Ile Leu Ile Thr Ser Leu Ile Gly Gly Gly Leu
        530                 535                 540

Leu Ile Leu Ile Ile Leu Thr Val Ala Tyr Gly Leu Lys Lys Pro Asn
545                 550                 555                 560

Lys Leu Thr His Leu Cys Trp Pro Thr Val Pro Asn Pro Ala Glu Ser
            565                 570                 575

Ser Ile Ala Thr Trp His Gly Asp Asp Phe Lys Asp Lys Leu Asn Leu
            580                 585                 590

Lys Glu Ser Asp Asp Ser Val Asn Thr Glu Asp Arg Ile Leu Lys Pro
            595                 600                 605

Cys Ser Thr Pro Ser Asp Lys Leu Val Ile Asp Lys Leu Val Val Asn
            610                 615                 620

Phe Gly Asn Val Leu Gln Glu Ile Phe Thr Asp Glu Ala Arg Thr Gly
625                 630                 635                 640

Gln Glu Asn Asn Leu Gly Gly Glu Lys Asn Gly Thr Arg Ile Leu Ser
                645                 650                 655

Ser Cys Pro Thr Ser Ile
            660

<210> SEQ ID NO 7
<211> LENGTH: 732
<212> TYPE: PRT
<213> ORGANISM: Homo sapiens
<220> FEATURE:
<221> NAME/KEY: SIGNAL
<222> LOCATION: (1)..(20)
<220> FEATURE:
<221> NAME/KEY: TRANSMEM
<222> LOCATION: (520)..(543)

<400> SEQUENCE: 7

Met Met Trp Thr Trp Ala Leu Trp Met Leu Pro Ser Leu Cys Lys Phe
1               5                   10                  15

Ser Leu Ala Ala Leu Pro Ala Lys Pro Glu Asn Ile Ser Cys Val Tyr
            20                  25                  30

Tyr Tyr Arg Lys Asn Leu Thr Cys Thr Trp Ser Pro Gly Lys Glu Thr
        35                  40                  45

Ser Tyr Thr Gln Tyr Thr Val Lys Arg Thr Tyr Ala Phe Gly Glu Lys
```

```
                50                  55                  60
His Asp Asn Cys Thr Thr Asn Ser Ser Thr Ser Glu Asn Arg Ala Ser
 65                  70                  75                  80

Cys Ser Phe Phe Leu Pro Arg Ile Thr Ile Pro Asp Asn Tyr Thr Ile
                 85                  90                  95

Glu Val Glu Ala Glu Asn Gly Asp Gly Val Ile Lys Ser His Met Thr
                100                 105                 110

Tyr Trp Arg Leu Glu Asn Ile Ala Lys Thr Glu Pro Pro Lys Ile Phe
                115                 120                 125

Arg Val Lys Pro Val Leu Gly Ile Lys Arg Met Ile Gln Ile Glu Trp
                130                 135                 140

Ile Lys Pro Glu Leu Ala Pro Val Ser Ser Asp Leu Lys Tyr Thr Leu
145                 150                 155                 160

Arg Phe Arg Thr Val Asn Ser Thr Ser Trp Met Glu Val Asn Phe Ala
                165                 170                 175

Lys Asn Arg Lys Asp Lys Asn Gln Thr Tyr Asn Leu Thr Gly Leu Gln
                180                 185                 190

Pro Phe Thr Glu Tyr Val Ile Ala Leu Arg Cys Ala Val Lys Glu Ser
                195                 200                 205

Lys Phe Trp Ser Asp Trp Ser Gln Glu Lys Met Gly Met Thr Glu Glu
210                 215                 220

Glu Ala Pro Cys Gly Leu Glu Leu Trp Arg Val Leu Lys Pro Ala Glu
225                 230                 235                 240

Ala Asp Gly Arg Arg Pro Val Arg Leu Leu Trp Lys Lys Ala Arg Gly
                245                 250                 255

Ala Pro Val Leu Glu Lys Thr Leu Gly Tyr Asn Ile Trp Tyr Tyr Pro
                260                 265                 270

Glu Ser Asn Thr Asn Leu Thr Glu Thr Met Asn Thr Thr Asn Gln Gln
                275                 280                 285

Leu Glu Leu His Leu Gly Gly Glu Ser Phe Trp Val Ser Met Ile Ser
290                 295                 300

Tyr Asn Ser Leu Gly Lys Ser Pro Val Ala Thr Leu Arg Ile Pro Ala
305                 310                 315                 320

Ile Gln Glu Lys Ser Phe Gln Cys Ile Glu Val Met Gln Ala Cys Val
                325                 330                 335

Ala Glu Asp Gln Leu Val Val Lys Trp Gln Ser Ser Ala Leu Asp Val
                340                 345                 350

Asn Thr Trp Met Ile Glu Trp Phe Pro Asp Val Asp Ser Glu Pro Thr
                355                 360                 365

Thr Leu Ser Trp Glu Ser Val Ser Gln Ala Thr Asn Trp Thr Ile Gln
                370                 375                 380

Gln Asp Lys Leu Lys Pro Phe Trp Cys Tyr Asn Ile Ser Val Tyr Pro
385                 390                 395                 400

Met Leu His Asp Lys Val Gly Glu Pro Tyr Ser Ile Gln Ala Tyr Ala
                405                 410                 415

Lys Glu Gly Val Pro Ser Glu Gly Pro Glu Thr Lys Val Glu Asn Ile
                420                 425                 430

Gly Val Lys Thr Val Thr Ile Thr Trp Lys Glu Ile Pro Lys Ser Glu
                435                 440                 445

Arg Lys Gly Ile Ile Cys Asn Tyr Thr Ile Phe Tyr Gln Ala Glu Gly
                450                 455                 460

Gly Lys Gly Phe Ser Lys Thr Val Asn Ser Ser Ile Leu Gln Tyr Gly
465                 470                 475                 480
```

```
Leu Glu Ser Leu Lys Arg Lys Thr Ser Tyr Ile Val Gln Val Met Ala
                485                 490                 495
Ser Thr Ser Ala Gly Gly Thr Asn Gly Thr Ser Ile Asn Phe Lys Thr
            500                 505                 510
Leu Ser Phe Ser Val Phe Glu Ile Ile Leu Ile Thr Ser Leu Ile Gly
        515                 520                 525
Gly Gly Leu Leu Ile Leu Ile Ile Leu Thr Val Ala Tyr Gly Leu Lys
    530                 535                 540
Lys Pro Asn Lys Leu Thr His Leu Cys Trp Pro Thr Val Pro Asn Pro
545                 550                 555                 560
Ala Glu Ser Ser Ile Ala Thr Trp His Gly Asp Asp Phe Lys Asp Lys
                565                 570                 575
Leu Asn Leu Lys Glu Ser Asp Asp Ser Val Asn Thr Glu Asp Arg Ile
            580                 585                 590
Leu Lys Pro Cys Ser Thr Pro Ser Asp Lys Leu Val Ile Asp Lys Leu
        595                 600                 605
Val Val Asn Phe Gly Asn Val Leu Gln Glu Ile Phe Thr Asp Glu Ala
    610                 615                 620
Arg Thr Gly Gln Glu Asn Asn Leu Gly Gly Lys Asn Gly Tyr Val
625                 630                 635                 640
Thr Cys Pro Phe Arg Pro Asp Cys Pro Leu Gly Lys Ser Phe Glu Glu
                645                 650                 655
Leu Pro Val Ser Pro Glu Ile Pro Pro Arg Lys Ser Gln Tyr Leu Arg
            660                 665                 670
Ser Arg Met Pro Glu Gly Thr Arg Pro Glu Ala Lys Glu Gln Leu Leu
        675                 680                 685
Phe Ser Gly Gln Ser Leu Val Pro Asp His Leu Cys Glu Glu Gly Ala
    690                 695                 700
Pro Asn Pro Tyr Leu Lys Asn Ser Val Thr Ala Arg Glu Phe Leu Val
705                 710                 715                 720
Ser Glu Lys Leu Pro Glu His Thr Lys Gly Glu Val
                725                 730

<210> SEQ ID NO 8
<211> LENGTH: 4
<212> TYPE: PRT
<213> ORGANISM: Artificial
<220> FEATURE:
<223> OTHER INFORMATION: An artificially synthesized peptide sequence

<400> SEQUENCE: 8

Gly Gly Gly Ser
1

<210> SEQ ID NO 9
<211> LENGTH: 4
<212> TYPE: PRT
<213> ORGANISM: Artificial
<220> FEATURE:
<223> OTHER INFORMATION: An artificially synthesized peptide sequence

<400> SEQUENCE: 9

Ser Gly Gly Gly
1

<210> SEQ ID NO 10
<211> LENGTH: 5
<212> TYPE: PRT
```

```
<213> ORGANISM: Artificial
<220> FEATURE:
<223> OTHER INFORMATION: An artificially synthesized peptide sequence

<400> SEQUENCE: 10

Gly Gly Gly Gly Ser
1               5

<210> SEQ ID NO 11
<211> LENGTH: 5
<212> TYPE: PRT
<213> ORGANISM: Artificial
<220> FEATURE:
<223> OTHER INFORMATION: An artificially synthesized peptide sequence

<400> SEQUENCE: 11

Ser Gly Gly Gly Gly
1               5

<210> SEQ ID NO 12
<211> LENGTH: 6
<212> TYPE: PRT
<213> ORGANISM: Artificial
<220> FEATURE:
<223> OTHER INFORMATION: An artificially synthesized peptide sequence

<400> SEQUENCE: 12

Gly Gly Gly Gly Gly Ser
1               5

<210> SEQ ID NO 13
<211> LENGTH: 6
<212> TYPE: PRT
<213> ORGANISM: Artificial
<220> FEATURE:
<223> OTHER INFORMATION: An artificially synthesized peptide sequence

<400> SEQUENCE: 13

Ser Gly Gly Gly Gly Gly
1               5

<210> SEQ ID NO 14
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 14

Gly Gly Gly Gly Gly Gly Ser
1               5

<210> SEQ ID NO 15
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 15

Ser Gly Gly Gly Gly Gly Gly
1               5

<210> SEQ ID NO 16
<211> LENGTH: 119
<212> TYPE: PRT
<213> ORGANISM: Mus musculus
```

<400> SEQUENCE: 16

Asp Val Gln Leu Arg Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Tyr Ser Gly Ser Thr Ser Tyr Asn Pro Ser Leu
    50                  55                  60

Lys Ser Arg Val Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Pro Met Ile Thr Thr Asp Trp Phe Phe Asp Val Trp Gly Ala Gly
            100                 105                 110

Thr Thr Val Thr Val Ser Ser
            115

<210> SEQ ID NO 17
<211> LENGTH: 107
<212> TYPE: PRT
<213> ORGANISM: Mus musculus

<400> SEQUENCE: 17

Asp Ile Val Met Thr Gln Ser Pro Ala Thr Leu Ser Val Thr Pro Gly
1               5                   10                  15

Asp Arg Val Ser Leu Ser Cys Arg Ala Ser His Asp Ile Ser Asp Phe
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Trp
                85                  90                  95

Thr Phe Gly Gly Gly Thr Lys Leu Glu Ile Lys
            100                 105

<210> SEQ ID NO 18
<211> LENGTH: 6
<212> TYPE: PRT
<213> ORGANISM: Mus musculus

<400> SEQUENCE: 18

Ser Asp Tyr Ala Trp Asn
1               5

<210> SEQ ID NO 19
<211> LENGTH: 15
<212> TYPE: PRT
<213> ORGANISM: Mus musculus

<400> SEQUENCE: 19

Tyr Ile Ser Tyr Ser Gly Ser Thr Ser Tyr Asn Pro Ser Leu Lys
1               5                   10                  15

-continued

```
<210> SEQ ID NO 20
<211> LENGTH: 10
<212> TYPE: PRT
<213> ORGANISM: Mus musculus

<400> SEQUENCE: 20

Met Ile Thr Thr Asp Trp Phe Phe Asp Val
1               5                   10

<210> SEQ ID NO 21
<211> LENGTH: 11
<212> TYPE: PRT
<213> ORGANISM: Mus musculus

<400> SEQUENCE: 21

Arg Ala Ser His Asp Ile Ser Asp Phe Leu His
1               5                   10

<210> SEQ ID NO 22
<211> LENGTH: 7
<212> TYPE: PRT
<213> ORGANISM: Mus musculus

<400> SEQUENCE: 22

Tyr Ala Ser Gln Ser Ile Ser
1               5

<210> SEQ ID NO 23
<211> LENGTH: 9
<212> TYPE: PRT
<213> ORGANISM: Mus musculus

<400> SEQUENCE: 23

Gln Asn Gly His Ser Phe Pro Trp Thr
1               5

<210> SEQ ID NO 24
<211> LENGTH: 735
<212> TYPE: PRT
<213> ORGANISM: Cynomolgus

<400> SEQUENCE: 24

Met Met Trp Thr Trp Ala Leu Trp Met Phe Pro Leu Leu Cys Lys Phe
1               5                   10                  15

Gly Leu Ala Ala Leu Pro Ala Lys Pro Glu Asn Ile Ser Cys Val Tyr
            20                  25                  30

Tyr Tyr Arg Lys Asn Leu Thr Cys Thr Trp Ser Pro Gly Lys Glu Thr
        35                  40                  45

Ser Tyr Thr Gln Tyr Thr Ala Lys Arg Thr Tyr Ala Phe Gly Lys Lys
    50                  55                  60

His Asp Asn Cys Thr Thr Ser Ser Ser Thr Ser Glu Asn Arg Ala Ser
65                  70                  75                  80

Cys Ser Phe Phe Leu Pro Arg Ile Thr Ile Pro Asp Asn Tyr Thr Ile
                85                  90                  95

Glu Val Glu Ala Glu Asn Gly Asp Gly Val Ile Lys Ser Asp Met Thr
            100                 105                 110

Cys Trp Arg Leu Glu Asp Ile Ala Lys Thr Pro Pro Glu Ile Phe
        115                 120                 125

Ser Val Lys Pro Val Leu Gly Ile Lys Arg Met Ile Arg Ile Glu Trp
    130                 135                 140

Ile Lys Pro Glu Leu Ala Pro Val Ser Ser Asp Leu Lys Tyr Ala Leu
```

-continued

```
                145                 150                 155                 160
Arg Phe Arg Thr Val Asn Ser Thr Ser Trp Met Glu Val Asn Phe Ala
                    165                 170                 175
Lys Asn Arg Lys Asp Thr Asn Gln Thr Tyr Asn Leu Met Gly Leu Gln
                    180                 185                 190
Ala Phe Thr Glu Tyr Val Val Ala Leu Arg Cys Ala Val Lys Glu Ser
                    195                 200                 205
Lys Phe Trp Ser Asp Trp Ser Gln Glu Lys Met Gly Met Thr Glu Glu
                    210                 215                 220
Glu Ala Pro Cys Gly Leu Glu Leu Trp Arg Val Leu Lys Pro Thr Glu
225                 230                 235                 240
Val Asp Gly Arg Arg Pro Val Arg Leu Leu Trp Lys Lys Ala Arg Gly
                    245                 250                 255
Ala Pro Val Leu Glu Lys Thr Leu Gly Tyr Asn Ile Trp Tyr Phe Pro
                    260                 265                 270
Glu Asn Asn Thr Asn Leu Thr Glu Thr Val Asn Thr Thr Asn Gln Gln
                    275                 280                 285
Leu Glu Leu His Leu Gly Gly Glu Ser Tyr Trp Val Ser Met Ile Ser
                    290                 295                 300
Tyr Asn Ser Leu Gly Lys Ser Pro Val Thr Thr Leu Arg Ile Pro Ala
305                 310                 315                 320
Ile Gln Glu Lys Ser Phe Arg Cys Ile Glu Val Met Gln Ala Cys Leu
                    325                 330                 335
Ala Glu Asp Gln Leu Val Val Lys Trp Gln Ser Ser Ala Leu Asp Val
                    340                 345                 350
Asn Thr Trp Met Ile Glu Trp Phe Pro Asp Met Asp Ser Glu His Pro
                    355                 360                 365
Thr Leu Ser Trp Glu Ser Val Ser Gln Ala Thr Asn Trp Thr Ile Gln
                    370                 375                 380
Gln Asp Lys Leu Lys Pro Phe Trp Cys Tyr Asn Ile Ser Val Tyr Pro
385                 390                 395                 400
Met Leu His Asp Lys Val Gly Glu Pro Tyr Ser Ile Gln Ala Tyr Ala
                    405                 410                 415
Lys Glu Gly Ile Pro Ser Lys Gly Pro Glu Thr Lys Val Glu Asn Ile
                    420                 425                 430
Gly Val Lys Thr Val Thr Ile Thr Trp Lys Glu Ile Pro Lys Ser Glu
                    435                 440                 445
Arg Lys Gly Ile Ile Cys Asn Tyr Thr Ile Phe Tyr Gln Ala Glu Gly
                    450                 455                 460
Gly Lys Gly Phe Ser Lys Thr Val Asn Ser Ser Ile Leu Gln Tyr Gly
465                 470                 475                 480
Leu Glu Ser Leu Lys Arg Lys Thr Ser Tyr Thr Val Arg Val Met Ala
                    485                 490                 495
Ser Thr Ser Ala Gly Gly Ile Asn Gly Thr Ser Ile Asn Phe Lys Thr
                    500                 505                 510
Leu Ser Phe Ser Val Phe Glu Ile Ile Leu Ile Thr Ser Leu Ile Gly
                    515                 520                 525
Gly Gly Leu Leu Ile Leu Ile Ile Leu Thr Val Ala Tyr Gly Leu Lys
                    530                 535                 540
Lys Pro Asn Lys Leu Thr His Leu Cys Trp Pro Ser Val Pro Asn Pro
545                 550                 555                 560
Ala Glu Ser Ser Ile Ala Thr Trp Arg Gly Asp Asp Phe Lys Asp Lys
                    565                 570                 575
```

```
Leu Asn Leu Lys Glu Ser Asp Ser Val Asn Thr Glu Asp Arg Ile
            580                 585                 590
Leu Lys Pro Cys Ser Thr Pro Ser Asp Lys Leu Val Ile Asp Lys Ser
        595                 600                 605
Val Val Asn Phe Gly Asn Val Leu Gln Glu Met Phe Thr Asp Glu Ala
    610                 615                 620
Arg Thr Gly Gln Glu Asn Asn Leu Gly Gly Glu Lys Asn Glu Tyr Val
625                 630                 635                 640
Thr His Pro Phe Arg Ala Asp Cys Pro Leu Gly Lys Ser Phe Glu Glu
                645                 650                 655
Leu Pro Val Ser Pro Glu Ile Pro Pro Arg Lys Ser Gln Tyr Leu Arg
            660                 665                 670
Ser Arg Met Pro Glu Gly Thr Cys Leu Glu Ala Glu Glu Gln Leu Leu
        675                 680                 685
Val Ser Gly Gln Ser Leu Glu Ser Leu Ala Pro Asp His Val Arg Glu
    690                 695                 700
Ala Ala Ala Pro Asn Pro Tyr Leu Lys Asn Ser Val Thr Thr Arg Glu
705                 710                 715                 720
Phe Leu Val Ser Gln Lys Leu Pro Glu His Thr Lys Gly Glu Val
                725                 730                 735
```

METHOD OF TREATING AN INFLAMMATORY DISEASE COMPRISING ADMINISTERING AN NR 10 ANTIBODY ANTAGONIST

Cross-Reference to Related Applications

This application is the National Stage of International Application Serial No. PCT/JP2007/061625, filed on Jun. 8, 2007, which claims the benefit of Japanese Application Serial No. 2006-160096, filed on Jun. 8, 2006.

TECHNICAL FIELD

The present invention relates to novel agents for preventing or treating inflammatory diseases, which comprise NR 10 antagonists as active ingredients. The present invention also relates to methods for preventing or treating inflammatory diseases, which use NR 10 antagonists.

BACKGROUND ART

Many cytokines are known as humoral factors involved in the growth and differentiation of various types of cells, or in the activation of differentiated mature cell functions. Cytokine-stimulated cells produce different types of cytokines, thereby forming networks of multiple cytokines in the body. Biological homeostasis is maintained by a delicate balance of the mutual regulation between cytokines in these networks. Many inflammatory diseases are thought to result from a failure of such cytokine networks. Thus, monoclonal antibody-based anti-cytokine therapy is drawing much attention. For example, anti-TNF antibodies and anti-IL-6 receptor antibodies have been demonstrated to be highly effective clinically. On the other hand, there are many examples of failure where no therapeutic effects were produced when a single cytokine, such as IL-4, was blocked alone, due to the activation of compensatory pathways in actual pathological conditions.

The present inventors succeeded in isolating a novel cytokine receptor NR 10 that was highly homologous to gp130, a receptor for IL-6 signal transduction (Patent Document 1). NR 10 forms a heterodimer with oncostatin M receptor (OSMR) and functions as an IL-31 receptor (Non-patent Document 1). Zymogenetics, Inc. reported that transgenic mice overexpressing IL-31 spontaneously developed pruritic dermatitis (Patent Document 2).

However, it cannot be asserted that the forced expression of a cytokine in mice or a high blood level of a cytokine in pathological model mice is indeed the cause of a disease. There is no information on whether any therapeutic effects are produced when a signal is blocked by an antibody. For example, pruritic dermatitis develops in transgenic mice in which IL-18 is overexpressed in keratinocytes. Furthermore, the blood IL-18 concentration elevates with the progression of pathological conditions in NC/Nga model mice for spontaneous atopic dermatitis. Based on the above findings, the overexpression of IL-18 was predicted to be the cause of disease. In reality however, the administration of neutralizing antibodies produced no therapeutic effects (Non-patent Document 2).

As described above, inhibition of the function of a cytokine does not necessarily produce therapeutic effects in diseases in which the expression level of a cytokine is elevated. Prediction of diseases on which therapeutic effects are actually produced is difficult to make based on the expression level of a cytokine. It is thus important to find diseases in which inhibition of signal transduction of a target cytokine actually produces therapeutic effects.

Prior art documents of the present invention are described below.

Patent Document 1: WO 00/75314
Patent Document 2: WO 03/060090
Non-patent Document 1: IL-31 is associated with cutaneous lymphocyte antigen-positive skin homing T cells in patients with atopic dermatitis, J Allergy Clin Immunol. 2006 February; 117(2): 418-25
Non-patent Document 2: Administration of anti-interleukin 18 antibody fails to inhibit development of dermatitis in atopic dermatitis-model mice NC/Nga, British Journal of Dermatology 149: 39-45, 2003

DISCLOSURE OF THE INVENTION

Problems to be Solved by the Invention

The present invention was achieved in view of the circumstances described above. An objective of the present invention is to provide cytokine receptor antagonist-based anti-cytokine therapies for inflammatory diseases. More specifically, the objective of the present invention is to discover inflammatory diseases in which a therapeutic effect may be obtained by anti-NR 10 neutralizing antibodies, and to provide novel methods for treating such diseases. Another objective of the present invention is to provide anti-human NR 10 neutralizing antibodies that are clinically applicable to humans.

Means for Solving the Problems

The present inventors conducted dedicated studies to solve the above-described objectives. The present inventors tried to assess the drug efficacy of anti-mouse NR 10 neutralizing antibodies in mouse models for various pathological conditions. The results demonstrated that the neutralizing antibodies produced the effect of markedly suppressing symptoms in atopic dermatitis model mice using NC/Nga mice, and in model mice for chronic dermatitis, which were developed by repeated application of picryl chloride. This proved that the neutralizing antibodies were actually useful as a therapeutic agent. In addition, the antibodies were demonstrated to produce the effect of suppressing symptoms in collagen arthritis, a model for rheumatism, and in collagenase arthritis, a model for osteoarthritis. These results suggest that the NR 10-neutralizing antibody of the present invention can be used to prevent or treat chronic inflammation. The present inventors also succeeded in obtaining human NR 10 neutralizing antibodies. Specifically, the present invention provides:

[1] an agent for preventing or treating an inflammatory disease, wherein the agent comprises an NR 10 antagonist as an active ingredient;
[2] the preventive or therapeutic agent of [1], wherein the NR 10 antagonist is an antibody having an NR 10 neutralizing activity;
[3] the preventive or therapeutic agent of [2], wherein the antibody is a monoclonal antibody;
[4] the preventive or therapeutic agent of [2], wherein the antibody is a monoclonal antibody having a human NR 10 neutralizing activity;
[5] the preventive or therapeutic agent of any one of [2] to [4], wherein the antibody is a recombinant antibody;
[6] the preventive or therapeutic agent of [5], wherein the recombinant antibody is a chimeric antibody, humanized antibody, or human antibody;

[7] the preventive or therapeutic agent of any one of [2] to [6], wherein the agent comprises as an active ingredient a fragment and/or a modified fragment of the antibody with NR 10 neutralizing activity;

[8] the preventive or therapeutic agent of any one of [1] to [7], wherein the inflammatory disease is atopic dermatitis;

[9] the preventive or therapeutic agent of any one of [1] to [7], wherein the inflammatory disease is chronic dermatitis;

[10] the preventive or therapeutic agent of any one of [1] to [7], wherein the inflammatory disease is rheumatism;

[11] the preventive or therapeutic agent of any one of [1] to [7], wherein the inflammatory disease is osteoarthritis;

[12] an antibody having an NR 10 neutralizing activity;

[13] the antibody of [12], which is a monoclonal antibody;

[14] the antibody of [12], wherein NR 10 is human NR 10;

[15] the antibody of any one of [12] to [14], which is a recombinant antibody;

[16] the antibody of [15], wherein the recombinant antibody is a chimeric antibody, humanized antibody, or human antibody;

[17] a fragment and/or a modified fragment of the antibody of any one of [12] to [16]

[18] a method for preventing or treating an inflammatory disease, which comprises the step of administering an NR 10 antagonist to a patient with an inflammatory disease; and

[19] use of an NR 10 antagonist to produce an agent for preventing or treating an inflammatory disease.

BRIEF DESCRIPTION OF THE DRAWINGS

FIG. 9 is a graph showing the correlation between the concentration of chimeric antibody NA633 against human NR 10 and cell growth-suppressing activity in the presence of IL-31. NA633 exhibited strong NR 10-neutralizing activity.

FIG. 10 is a diagram comparing the amino acid sequences of human NR 10 and NR 10 of a cynomolgus monkey. The double-underlined sequence indicates the transmembrane region.

FIG. 11 is a graph showing the cell growth-suppressing activity of the chimeric antibody NA633 in human-IL-31 stimulated cynomolgus monkey NR 10/human OSMR/BaF cell line. NA633 also showed cynomolgus monkey NR 10-neutralizing activity.

FIG. 12 is a graph showing the transition of percent body weight change in DSS colitis model mice.

BEST MODE FOR CARRYING OUT THE INVENTION

Figure 1:
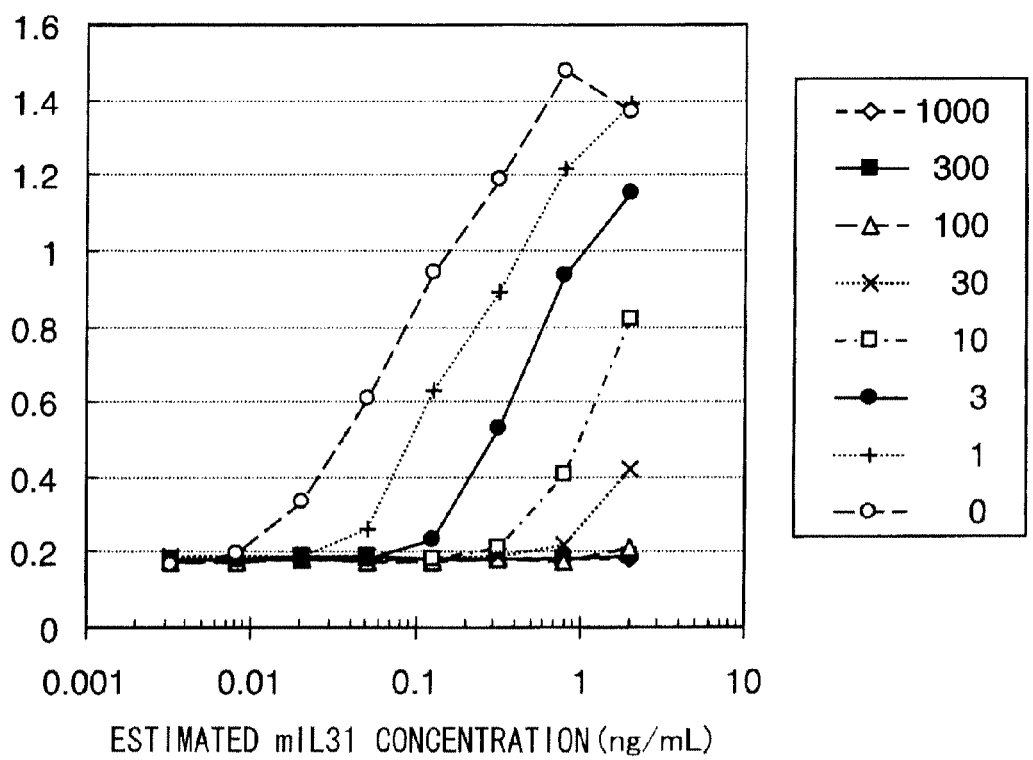
FIG. 1 is a graph showing a result obtained by observing the cell growth-suppressing effect of BM095 added to a cell growth assay system using IL-31-dependent Ba/F3 cells. The horizontal axis indicates estimated mIL-31 concentrations in the assay system, and the vertical axis indicates cell counts (OD450 (absorbance at 450 nm)). Amounts of BM095 added (unit: ng/ml) are shown in the legend. A cell-growth suppressing effect dependent on the amount of BM095 added was observed.

The present invention relates to agents for preventing or treating inflammatory diseases, which comprise NR 10 antagonists as active ingredients. The present invention is based on the present inventors' finding that NR 10 antagonists (for example, anti-NR 10 neutralizing antibodies) significantly suppress symptoms in model mice with atopic dermatitis, chronic dermatitis, rheumatism, osteoarthritis or such.

NR 10 is a protein that forms a heterodimer with oncostatin M receptor (OSMR), and functions as an IL-31 receptor. NR 10 is also known by other names, such as glm-r (J Biol Chem 277, 16831-6, 2002), GPL (J Biol Chem 278, 49850-9, 2003), and IL-31RA (Nat Immunol 5, 752-60, 2004). The NR 10 of the present invention includes proteins called by such names. The NR 10 of the present invention also includes NR 10 derived from humans, mice, and other mammals. Preferred NR 10 includes human- and mouse-derived NR 10, but is not limited thereto. There are multiple known splicing variants of human-derived NR 10 (WO 00/075314). Of the above-described splicing variants, NR 10.1 consists of 662 amino acids and comprises a transmembrane domain. NR 10.2 is a soluble receptor-like protein consisting of 252 amino acids without the transmembrane domain. Meanwhile, known NR 10 splicing variants that function as transmembrane receptor proteins include NR 10.3 and IL-31RAv3. The human NR 10 of the present invention is not particularly limited, as long as it forms a heterodimer with oncostatin M receptor (OSMR) and functions as an IL-31 receptor. Preferred NR 10 includes NR 10.3 (also referred to as ILRAv4 (Nat Immunol 5, 752-60, 2004)) and IL-31RAv3. NR 10.3 (IL-31RAv4) consists of 662 amino acids (WO 00/075314; Nat Immunol 5, 752-60, 2004) and IL-31RAv3 consists of 732 amino acids (GenBank Accession No: NM_139017). The amino acid sequence of IL-31RAv4 is shown in SEQ ID NO: 6, and the amino acid sequence of IL-31RAv3 is shown in SEQ ID NO: 7. Meanwhile, mouse-derived NR 10 includes proteins comprising the amino acid sequence of SEQ ID NO: 5.

The NR 10 antagonists of the present invention refer to substances that bind to NR 10 and block NR 10-activation-based intracellular signal transduction, thereby causing loss or suppression of physiological activities of cells. Herein, physiological activities include, for example, activities of inducing or suppressing the production of physiologically active substances (for example, chemokines and inflammatory cytokines), activities of enhancing or suppressing the secretion of the substances, growth activity, growth-inducing activity, survival activity, differentiation activity, differentiation-inducing activity, transcriptional activity, membrane transport activity, binding activity, proteolytic activity, phosphorylation/dephosphorylation activity, oxidation-reduction activity, transfer activity, nucleolytic activity, dehydration activity, cell-death-inducing activity, and apoptosis-inducing activity, but are not limited thereto.

The presence of antagonist activity can be determined by methods known to those skilled in the art. For example, test compounds are contacted with NR 10 expressed on the surface of cells in the presence of a ligand, and it is determined whether or not intracellular signal transduction, which is an indicator of NR 10 activation, is generated. Such a determination can be made, for example, by the method described in the document "Dillon S R, et al., Interleukin 31, a cytokine produced by activated T cells, induces dermatitis in mice. Nat. Immunol. 2004 July; 5(7):752-60". Compounds that inhibit intracellular signal transduction in response to ligand stimulation are thought to serve as NR 10 antagonists.

The antagonists of the present invention may be natural or artificial compounds. Known compounds may be used as the antagonists of the present invention. Novel compounds determined to have antagonist activity by the methods described above may also be used.

In an embodiment of the present invention, the NR 10 antagonists include antibodies having the activity of neutralizing NR 10. The "antibodies having NR 10-neutralizing activity" of the present invention refer to antibodies having the activity of suppressing NR 10-based physiological activities. The "antibodies having NR 10-neutralizing activity" of the present invention may be polyclonal or monoclonal antibodies, and as a preferred embodiment, includes monoclonal antibodies.

Such monoclonal antibodies having NR 10-neutralizing activity, can be obtained, for example, by the following procedure: anti-NR 10 monoclonal antibodies are prepared by using as an antigen NR 10 or a fragment thereof that is derived from a mammal, such as human or mouse, by known methods, and then antibodies having NR 10-neutralizing activity are selected from the thus obtained anti-NR 10 monoclonal antibodies. Specifically, immunization is achieved by conventional immunization methods using as a sensitizing antigen a desired antigen or cells expressing the desired antigen. Anti-NR 10 monoclonal antibodies can be prepared by fusing the obtained immune cells with known parental cells using conventional cell fusion methods, and screening them for monoclonal antibody-producing cells (hybridomas) by conventional screening methods. Animals to be immunized include, for example, mammals, such as mice, rats, rabbits, sheep, monkeys, goats, donkeys, cows, horses, and pigs. The antigen can be prepared using the known NR 10 gene sequence according to known methods, for example, by methods using baculovirus (for example, WO 98/46777). As described in Examples herein below, antibodies having NR 10-neutralizing activity may be selected, for example, by testing the effect of suppressing the growth of an IL-31-dependent cell line after the candidate antibody is added to cells of the IL-31-dependent cell line. Antibodies that suppress the growth of IL-31-dependent cell line in the method described above are considered to have NR 10-neutralizing activity.

Hybridomas can be prepared, for example, according to the method of Milstein et al. (Kohler, G. and Milstein, C., Methods Enzymol. (1981) 73: 3-46) or such. When the immunogenicity of an antigen is low, immunization may be performed after linking the antigen with a macromolecule having immunogenicity, such as albumin.

In a preferred embodiment of the present invention, antibodies having NR 10-neutralizing activity include monoclonal antibodies having the activity of neutralizing human NR 10. There is no particular limitation on the immunogen for preparing monoclonal antibodies having the activity of neutralizing human NR 10, as long as it allows preparation of antibodies having the activity of neutralizing human NR 10. For example, multiple variants of human NR 10 are known to exist. Any of the variants may be used as immunogens, as long as it allows preparation of antibodies having human NR 10 neutralizing activity. Alternatively, a peptide fragment of NR 10 or a natural NR 10 sequence introduced with artificial mutations may be used as the immunogen under the same conditions. Human NR 10.3 is a preferred immunogen to prepare antibodies of the present invention that have NR 10-neutralizing activity.

Herein, the above-described antibodies of the present invention are not particularly limited, as long as they have NR 10-neutralizing activity. The antibodies also include recombinant antibodies such as chimeric antibodies, humanized antibodies, and human antibodies. The chimeric antibodies comprise, for example, the heavy and light chain constant regions of a human antibody, and the heavy and light chain variable regions of a non-human mammal, such as mouse. The chimeric antibodies can be produced by known methods. For example, the antibodies can be produced by cloning an antibody gene from hybridomas, inserting it into an appropriate vector, and introducing the construct into hosts (see, for example, Carl, A. K. Borrebaeck, James, W. Larrick, THERAPEUTIC MONOCLONAL ANTIBODIES, Published in the United Kingdom by MACMILLAN PUBLISHERS LTD, 1990). Specifically, cDNAs of the antibody variable regions (V regions) are synthesized from mRNA of hybridomas using reverse transcriptase. Once DNAs encoding the V regions of an antibody of interest are obtained, these are linked with DNAs encoding the constant regions (C regions) of a desired human antibody. The resulting constructs are inserted into expression vectors. Alternatively, the DNAs encoding the antibody V regions may be inserted into expression vectors comprising DNAs encoding the C regions of a human antibody. The DNAs are inserted into expression vectors so that they are expressed under the regulation of the expression regulatory regions, for example, enhancers and promoters. In the next step, host cells can be transformed with the expression vectors to allow expression of chimeric antibodies.

A humanized antibody, which is also called a reshaped human antibody, is obtained by transferring a complementarity determining region (CDR) of an antibody of a nonhuman mammal such as a mouse, with the CDR of a human antibody. Conventional genetic recombination techniques for the preparation of such antibodies are also known. Specifically, a DNA sequence designed to ligate a CDR of a mouse antibody with the framework regions (FRs) of a human antibody is synthesized by PCR, using several oligonucleotides constructed to comprise overlapping portions at their ends. A humanized antibody can be obtained by (1) ligating the resulting DNA to a DNA that encodes a human antibody constant region; (2) incorporating this into an expression vector; and (3) transfecting the vector into a host to produce the antibody (see European Patent Application No. EP 239, 400 and International Patent Application Publication No. WO 96/02576). Human antibody FRs that are ligated via the CDR are selected where the CDR forms a favorable antigen-binding site. As necessary, amino acids in the framework region of an antibody variable region may be substituted such that the CDR of a reshaped human antibody forms an appropriate antigen-binding site (Sato, K. et al., Cancer Res. (1993) 53, 851-856).

Methods for obtaining human antibodies are also known. For example, desired human antibodies with antigen-binding activity can be obtained by (1) sensitizing human lymphocytes with antigens of interest or cells expressing antigens of interest in vitro; and (2) fusing the sensitized lymphocytes with human myeloma cells such as U266 (see Japanese Patent Application Kokoku Publication No. (JP-B) H01-59878 (examined, approved Japanese patent application published for opposition)). Alternatively, the desired human antibody can also be obtained by using a desired antigen to immunize a transgenic animal that comprises an entire repertoire of human antibody genes (see International Patent Application Publication Nos. WO 93/12227, WO 92/03918, WO 94/02602, WO 94/25585, WO 96/34096, and WO 96/33735).

Furthermore, techniques to obtain human antibodies by panning with a human antibody phage library are known. For example, the variable region of a human antibody is expressed as a single chain antibody (scFv) on the surface of a phage, using a phage display method, and phages that bind to the antigen can be selected. By analyzing the genes of selected phages, the DNA sequences encoding the variable regions of human antibodies that bind to the antigen can be determined. If the DNA sequences of scFvs that bind to the antigen are identified, appropriate expression vectors comprising these sequences can be constructed to obtain human antibodies. Such methods are well known (see WO 92/01047, WO 92/20791, WO 93/06213, WO 93/11236, WO 93/19172, WO 95/01438, and WO 95/15388).

The amino acid sequence of the heavy chain variable region or light chain variable region may be an amino acid sequence with a substitution, deletion, addition, and/or insertion of one or more amino acids in the amino acid sequence of the heavy chain variable region or light chain variable region of an antibody that has been confirmed to have NR 10-neutralizing activity, as long as NR 10-neutralizing activity is retained. Methods well known to those skilled in the art to prepare the amino acid sequence of the heavy chain variable region or light chain variable region of the antibody having NR 10-neutralizing activity, which comprises a substitution, deletion, addition, and/or insertion of one or more amino acids in the amino acid sequence of the heavy chain variable region or light chain variable region, include known methods for introducing mutations into proteins. For example, those skilled in the art can prepare mutants functionally equivalent to the heavy chain variable region or light chain variable region of the antibody having NR 10-neutralizing activity by introducing appropriate mutations into the amino acid sequence of the heavy chain variable region or light chain variable region of the antibody having NR 10-neutralizing activity using site-directed mutagenesis (Hashimoto-Gotoh, T, Mizuno, T, Ogasahara, Y, and Nakagawa, M. (1995) An oligodeoxyribonucleotide-directed dual amber method for site-directed mutagenesis. Gene 152, 271-275, Zoller, M J, and Smith, M. (1983) Oligonucleotide-directed mutagenesis of DNA fragments cloned into M13 vectors. Methods Enzymol. 100, 468-500, Kramer, W, Drutsa, V, Jansen, H W, Kramer, B, Pflugfelder, M, and Fritz, H J (1984) The gapped duplex DNA approach to oligonucleotide-directed mutation construction. Nucleic Acids Res. 12, 9441-9456, Kramer W, and Fritz H J (1987) Oligonucleotide-directed construction of mutations via gapped duplex DNA Methods. Enzymol. 154, 350-367, Kunkel, T A (1985) Rapid and efficient site-specific mutagenesis without phenotypic selection. Proc Natl Acad Sci USA. 82, 488-492) or the like. Thus, heavy chain variable regions or light chain variable regions that comprise mutations at one or more amino acids in the heavy chain variable region or light chain variable region of the antibody having NR 10-neutralizing activity are also included in the heavy chain variable region or light chain variable region of the present invention.

When an amino acid residue is altered, the amino acid is preferably mutated for a different amino acid(s) that conserves the properties of the amino acid side-chain. Examples of amino acid side chain properties are: hydrophobic amino acids (A, I, L, M, F, P, W, Y, and V), hydrophilic amino acids (R, D, N, C, E, Q, G, H, K, S, and T), amino acids comprising aliphatic side chains (G, A, V, L, I, and P), amino acids comprising hydroxyl group-containing side chains (S, T, and Y), amino acids comprising sulfur-containing side chains (C and M), amino acids comprising carboxylic acid- and amide-containing side chains (D, N, E, and Q), amino acids comprising basic side chains (R, K, and H), and amino acids comprising aromatic side chains (H, F, Y, and W) (amino acids are represented by one-letter codes in parentheses). Amino acid substitutions within each group are called conservative substitutions. It is already known that a polypeptide comprising a modified amino acid sequence in which one or more amino acid residues in a given amino acid sequence are deleted, added, and/or substituted with other amino acids can retain the original biological activity (Mark, D. F. et al., Proc. Natl. Acad. Sci. USA; (1984) 81:5662-6; Zoller, M. J. and Smith, M., Nucleic Acids Res. (1982) 10:6487-500; Wang, A. et al., Science (1984) 224:1431-3; Dalbadie-McFarland, G. et al., Proc. Natl. Acad. Sci. USA (1982) 79:6409-13). Such mutants comprise an amino acid sequence which is at least 70% identical to the amino acid sequence of a heavy chain variable region or light chain variable region of the present invention, more preferably at least 75%, even more preferably at least 80%, still more preferably at least 85%, yet more preferably at least 90%, and most preferably at least 95% identical. Herein, sequence identity is defined as the percentage of residues identical to those in the original amino acid sequence of the heavy chain variable region or light chain variable region, determined after the sequences are aligned and gaps are appropriately introduced to maximize the sequence identity as necessary. The identity of amino acid sequences can be determined by the method described above.

Alternatively, an amino acid sequence of the heavy chain variable region or light chain variable region that comprises a substitution, deletion, addition, and/or insertion of one or more amino acids in the amino acid sequence of the heavy chain variable region or light chain variable region and retains NR 10-neutralizing activity can be obtained from nucleic acid that hybridizes under stringent conditions to nucleic acid comprising the nucleotide sequence encoding the amino acid sequence of the heavy chain variable region or light chain variable region. Stringent hybridization conditions to isolate a nucleic acid that hybridizes under stringent conditions to a nucleic acid that comprises the nucleotide sequence encoding the amino acid sequence of the heavy chain variable region or light chain variable region include, for example, the conditions of 6M urea, 0.4% SDS, 0.5×SSC, and 37° C., or hybridization conditions with stringencies equivalent thereto. With more stringent conditions, for example, the conditions of 6M urea, 0.4% SDS, 0.1×SSC, and 42° C., isolation of nucleic acids with a much higher homology can be expected. The sequences of the isolated nucleic acids can be determined by the known methods described below. The overall nucleotide sequence homology of the isolated nucleic acid is at least 50% or higher sequence identity, preferably 70% or higher, more preferably 90% or higher (for example, 95%, 96%, 97%, 98%, 99%, or higher).

A nucleic acid that hybridizes under stringent conditions to a nucleic acid comprising the nucleotide sequence encoding the amino acid sequence of the heavy chain variable region or light chain variable region can also be isolated using, instead of the above-described methods using hybridization techniques, gene amplification methods using primers synthesized based on the information of nucleotide sequence encoding the amino acid sequence of the heavy chain variable region or light chain variable region, for example, polymerase chain reaction (PCR).

Specifically, the identity of one nucleotide sequence or amino acid sequence to another can be determined using the algorithm BLAST, by Karlin and Altschul (Proc. Natl. Acad. Sci. USA (1993) 90, 5873-7). Programs such as BLASTN and BLASTX were developed based on this algorithm (Altschul et al., J. Mol. Biol. (1990) 215, 403-10). To analyze nucleotide sequences according to BLASTN based on BLAST, the parameters are set, for example, as score=100 and wordlength=12. On the other hand, parameters used for the analysis of amino acid sequences by BLASTX based on BLAST include, for example, score=50 and wordlength=3. Default parameters for each program are used when using the BLAST and Gapped BLAST programs. Specific techniques for such analyses are known in the art (see the website of the National Center for Biotechnology Information (NCBI), Basic Local Alignment Search Tool (BLAST).

Alternatively, the antibodies of the present invention may be minibodies. Such minibodies of the present invention include antibody fragments lacking some portions of a whole antibody (for example, whole IgG), and are not particularly limited as long as they retain NR 10-neutralizing activity. The minibodies of the present invention are not particularly limited, as long as they are portions of whole antibodies. The minibodies preferably comprise a heavy chain variable region (VH) or light chain variable region (VL). Particularly preferred minibodies comprise both VH and VL.

The minibodies of the present invention preferably have a smaller molecular weight than whole antibodies. However, the minibodies may form multimers, for example, dimers, trimers, or tetramers, and thus their molecular weights can be greater than those of whole antibodies.

The minibodies of the present invention include, for example, scFv antibodies. ScFv antibodies are single-chain polypeptides constructed by linking a heavy chain variable region ([VH]) and a light chain variable region ([VL]) via a linker or such (Huston, J. S. et al., Proc. Natl. Acad. Sci. U.S.A. (1988) 85, 5879-5883; Plickthun "The Pharmacology of Monoclonal Antibodies" Vol. 113, eds., Resenburg and Moore, Springer Verlag, New York, pp. 269-315, (1994)). The order of the heavy chain variable region and light chain variable region to be linked together is not particularly limited, and they may be arranged in any order. Examples of the arrangements are listed below.

[VH] linker [VL]
[VL] linker [VH]

The amino acid sequence of the heavy chain variable region or light chain variable region may comprise a substitution, deletion, addition, and/or insertion. Furthermore, the heavy chain variable region and light chain variable region may also lack some portions or be added with other polypeptides, as long as they have antigen binding ability when linked together. Alternatively, the variable regions may be chimerized or humanized.

In the present invention, linkers which bind the variable region of the antibody comprise arbitrary peptide linkers that can be introduced using genetic engineering, or synthetic linkers (for example, linkers disclosed in "Protein Engineering, 9(3), 299-305, 1996").

The preferred linkers in the present invention are peptide linkers. The lengths of the peptide linkers are not particularly limited and those skilled in the art can appropriately select the lengths depending on the purpose. Typical lengths are one to 100 amino acids, preferably 3 to 50 amino acids, more preferably 5 to 30 amino acids, and particularly preferably 12 to 18 amino acids (for example, 15 amino acids).

Amino acid sequences of such peptide linkers include, for example:

```
Ser

Gly·Ser

Gly·Gly·Ser

Ser·Gly·Gly

Gly·Gly·Gly·Ser            (SEQ ID NO: 8)

Ser·Gly·Gly·Gly            (SEQ ID NO: 9)

Gly·Gly·Gly·Gly·Ser        (SEQ ID NO: 10)

Ser·Gly·Gly·Gly·Gly        (SEQ ID NO: 11)

Gly·Gly·Gly·Gly·Gly·Ser    (SEQ ID NO: 12)

Ser·Gly·Gly·Gly·Gly·Gly    (SEQ ID NO: 13)

Gly·Gly·Gly·Gly·Gly·Gly·Ser (SEQ ID NO: 14)

Ser·Gly·Gly·Gly·Gly·Gly·Gly (SEQ ID NO: 15)

(Gly·Gly·Gly·Gly·Ser (SEQ ID NO: 10))n (Ser·Gly·Gly·Gly·Gly (SEQ ID NO: 11))n
``` where n is an integer of 1 or larger.

Synthetic linkers (chemical crosslinking agents) include crosslinking agents that are routinely used to crosslink peptides, for example, N-hydroxy succinimide (NHS), disuccinimidyl suberate (DSS), bis(sulfosuccinimidyl) suberate ($BS^3$), dithiobis(succinimidyl propionate) (DSP), dithiobis (sulfosuccinimidyl propionate) (DTSSP), ethylene glycol bis (succinimidyl succinate) (EGS), ethylene glycol bis(sulfosuccinimidyl succinate) (sulfo-EGS), disuccinimidyl tartrate (DST), disulfosuccinimidyl tartrate (sulfo-DST), bis[2-(succinimidoxycarbonyloxy)ethyl] sulfone (BSOCOES), and bis [2-(sulfosuccinimidoxycarbonyloxy)ethyl] sulfone (sulfo-BSOCOES). These crosslinking agents are commercially available.

Antibodies of the present invention include antibodies in which two or more amino acid residues have been added to the amino acid sequence of an antibody of the present invention. Further, fusion proteins which result from a fusion between one of the above antibodies and a second peptide or protein is included in the present invention. The fusion proteins can be prepared by ligating a polynucleotide encoding an antibody of the present invention and a polynucleotide encoding a second peptide or polypeptide in frame, inserting this into an expression vector, and expressing the fusion construct in a host. Some techniques known to those skilled in the art are available for this purpose. The partner peptide or polypeptide to be fused with an antibody of the present invention may be a known peptide, for example, FLAG (Hopp, T. P. et al., BioTechnology 6, 1204-1210 (1988)), 6×His consisting of six His (histidine) residues, 10×His, influenza hemagglutinin (HA), human c-myc fragment, VSV-GP fragment, p18HIV fragment, T7-tag, HSV-tag, E-tag, SV40 T antigen fragment, lck tag, α-tubulin fragment, B-tag, Protein C fragment. Other partner polypeptides to be fused with the antibodies of the present invention include, for example, GST (glutathione-S-transferase), HA (influenza hemagglutinin), immunoglobulin constant region, β-galactosidase, and MBP (maltose-binding protein). A polynucleotide encoding one of these commercially available peptides or polypeptides can be fused with a polynucleotide encoding an antibody of the present invention. The fusion polypeptide can be prepared by expressing the fusion construct.

The antibodies of the present invention may differ in amino acid sequence, molecular weight, isoelectric point, presence/absence of sugar chains, and conformation depending on the cell or host producing the antibody, or purification method. However, a resulting antibody is included in the present invention, as long as it is functionally equivalent to an antibody of the present invention. For example, when an antibody of the present invention is expressed in prokaryotic cells, for example E. coli, a methionine residue is added to the N terminus of the original antibody amino acid sequence. Such antibodies are included in the present invention.

The antibody of the present invention can be prepared by methods known to those skilled in the art. The antibody can be prepared, for example, by genetic recombination techniques known to those skilled in the art based on the sequence of an antibody that recognizes NR 10. Specifically, such antibody can be prepared by constructing a polynucleotide encoding an antibody based on the sequence of an antibody that recognizes NR 10, inserting the construct into an expression vector, and then expressing it in appropriate host cells (see for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; Bird, R. E. and Walker, B. W., Trends Biotechnol. (1991) 9, 132-137).

The vectors include M13 vectors, pUC vectors, pBR322, pBluescript, and pCR-Script. Alternatively, when aiming to subclone and excise cDNA, the vectors include, for example, pGEM-T, pDIRECT, and pT7, in addition to the vectors described above. Expression vectors are particularly useful when using vectors for producing the antibodies of the present invention. For example, when aiming for expression in E. coli such as JM109, DH5α, HB101, and XL1-Blue, the expression vectors not only have the above-described characteristics that allow vector amplification in E. coli, but must also carry a promoter that allows efficient expression in E. coli, for example, lacZ promoter (Ward et al., Nature (1989) 341, 544-546; FASEB J. (1992) 6, 2422-2427), araB promoter (Better et al., Science (1988) 240, 1041-1043), T7 promoter or such. Such vectors include pGEX-5X-1 (Pharmacia), "QIAexpress system" (Quiagen), pEGFP, or pET (in this case, the host is preferably BL21 that expresses T7 RNA polymerase) in addition to the vectors described above.

The vectors may comprise signal sequences for antibody secretion. As a signal sequence for antibody secretion, a pelB signal sequence (Lei, S. P. et al J. Bacteriol. (1987) 169, 4379) may be used when a protein is secreted into the E. coli periplasm. The vector can be introduced into host cells by calcium chloride or electroporation methods, for example.

In addition to vectors for E. coli, the vectors for producing the antibodies of the present invention include mammalian expression vectors (for example, pcDNA3 (Invitrogen), pEF-BOS (Nucleic Acids. Res. 1990, 18(17), p 5322), pEF, and pCDM8), insect cell-derived expression vectors (for example, the "Bac-to-BAC baculovirus expression system" (Gibco-BRL) and pBacPAK8), plant-derived expression vectors (for example, pMH1 and pMH2), animal virus-derived expression vectors (for example, pHSV, pMV, and pAdex-Lcw), retroviral expression vectors (for example, pZIPneo), yeast expression vectors (for example, "Pichia Expression Kit" (Invitrogen), pNV11, and SP-Q01), and Bacillus subtilis expression vectors (for example, pPL608 and pKTH50), for example.

When aiming for expression in animal cells such as CHO, COS, and NIH3T3 cells, the vectors must have a promoter essential for expression in cells, for example, SV40 promoter (Mulligan et al., Nature (1979) 277, 108), MMLV-LTR promoter, EF1α promoter (Mizushima et al., Nucleic Acids Res. (1990) 18, 5322), and CMV promoter, and more preferably they have a gene for selecting transformed cells (for example, a drug resistance gene that allows evaluation using an agent (neomycin, G418, or such). Vectors with such characteristics include pMAM, pDR2, pBK-RSV, pBK-CMV, pOPRSV, and pOP13, for example.

In addition, the following method can be used for stable gene expression and gene amplification in cells: CHO cells deficient in a nucleic acid synthesis pathway are introduced with a vector (for example, pSV2-dhfr (Molecular Cloning $2^{nd}$ edition, Cold Spring Harbor Laboratory Press, 1989)) that carries a DHFR gene which compensates for the deficiency, and the vector is amplified using methotrexate (MTX). Alternatively, the following method can be used for transient gene expression: COS cells with a gene expressing SV40 T antigen on their chromosome are transformed with a vector (pcD and such) with an SV40 replication origin. Replication origins derived from polyoma virus, adenovirus, bovine papilloma virus (BPV), and such can also be used. To amplify gene copy number in host cells, the expression vectors may further carry selection markers such as aminoglycoside transferase (APH) gene, thymidine kinase (TK) gene, E. coli xanthine-guanine phosphoribosyltransferase (Ecogpt) gene, and dihydrofolate reductase (dhfr) gene.

Desired antibodies obtained by the methods described above can be isolated from inside host cells or from outside the cells (the medium, or such), and purified to homogeneity. The antibodies can be isolated and purified by methods routinely used for isolating and purifying antibodies, and the type of method is not limited. For example, the antibodies can be isolated and purified by appropriately selecting and combining column chromatography, filtration, ultrafiltration, salting out, solvent precipitation, solvent extraction, distillation, immunoprecipitation, SDS-polyacrylamide gel electrophoresis, isoelectrofocusing, dialysis, recrystallization, and such.

The chromatographies include, for example, affinity chromatography, ion exchange chromatography, hydrophobic chromatography, gel filtration, reverse phase chromatography, and adsorption chromatography (Strategies for Protein Purification and Characterization: A Laboratory Course Manual. Ed Daniel R. Marshak et al., Cold Spring Harbor Laboratory Press, 1996). The chromatographic methods described above can be conducted using liquid chromatography, for example, HPLC and FPLC. Columns that can be used for affinity chromatography include protein A columns and protein G columns. Columns using protein A include, for example, Hyper D, POROS, and Sepharose FF (GE Amersham Biosciences). The present invention comprises antibodies that are highly purified using these purification methods.

The present invention also provides agents for preventing or treating inflammatory diseases, which comprise as active ingredients fragments and/or modification products of an antibody of the present invention. The fragments and/or modification products of antibodies of the present invention include antibody fragments lacking some portions of the antibodies of the present invention (whole antibodies (for example, whole IgG), recombinant antibodies (for example, chimeric antibodies, humanized antibodies, and human antibodies), and minibodies (for example, scFv antibodies)), and are not particularly limited as long as they retain the ability to bind to their antigens. The antibody fragments of the present invention are not particularly limited, as long as they are portions of whole antibodies. The fragments preferably comprise a heavy chain variable region (VH) and/or a light chain variable region (VL). The amino acid sequence of the VH or VL may comprise substitutions, deletions, additions, and/or insertions. The VH and/or VL may lack some portions, as long as the ability to bind to the antigen is retained. Furthermore, the variable region may be chimerized or humanized. Specifically, antibody fragments include, for example, Fab, Fab', F(ab')2, and Fv. Such antibody fragments can be obtained by constructing genes encoding the antibody fragments, introducing them into expression vectors, and then expressing them in appropriate host cells (see for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; Bird, R. E. and Walker, B. W., Trends Biotechnol. (1991) 9, 132-137).

Furthermore, the antibodies of the present invention may be conjugated antibodies which are linked to any of various molecules, such as polyethylene glycol (PEG), radioactive substances, fluorescent substances, luminescent substances, enzymes, and toxins. Such conjugated antibodies can be obtained by chemically modifying the obtained antibodies. Methods for modifying antibodies have been established in this field (for example, U.S. Pat. Nos. 5,057,313 and 5,156,840). The "antibodies" of the present invention also include such conjugated antibodies.

The antibody's activity of binding to NR 10 can be determined by methods known to those skilled in the art. Methods for determining the antigen-binding activity of an antibody include, for example, ELISA (enzyme-linked immunosorbent assay), EIA (enzyme immunoassay), RIA (radioimmunoassay), and fluorescent antibody method. For example, when enzyme immunoassay is used, antibody-containing samples, such as purified antibodies and culture supernatants of antibody-producing cells, are added to antigen-coated plates. A secondary antibody labeled with an enzyme, such as alkaline phosphatase, is added and the plates are incubated. After washing, an enzyme substrate, such as p-nitrophenyl phosphate, is added, and the absorbance is measured to evaluate the antigen-binding activity.

Furthermore, the NR 10-neutralizing activity of an antibody can be determined, for example, by the method described in Examples, which involves testing the effect of suppressing the growth of the IL-31-dependent cell line.

The NR 10 antagonists or antibodies having NR 10-neutralizing activity of the present invention can be used in the agents for preventing or treating inflammatory diseases. The present inventors proved that administration of mouse NR 10 neutralizing antibodies produced marked therapeutic effects in model animals for various inflammatory diseases. Furthermore, the expression of human NR 10 has been reported to be enhanced in thickened epidermis of atopic dermatitis patients (Non-patent Document 1). The present inventors confirmed by immunohistochemical staining that, as with the case of humans, the expression of mouse NR 10 was enhanced in thickened epidermis of auricles in the above-described chronic dermatitis model mice (Example 5). These findings suggest that NR 10 is similarly involved in inflammatory diseases in all animal species, and that, like mouse NR 10 neutralizing antibodies, antibodies neutralizing human NR 10 are effective in preventing and treating various inflammatory diseases. Furthermore, as with the findings described in this Example, NR 10 antagonists other than antibodies are also expected to have therapeutic effects on various inflammatory diseases.

In the present invention, inflammatory disease refers to diseases with pathological features involved in cytological and histological reactions that occur in affected blood vessels and adjacent tissues in response to an injury or abnormal stimulation caused by physical, chemical, or biological agents (Stedman's Medical Dictionary, 5th Ed., MEDICAL VIEW CO., 2005). Generally, inflammatory diseases include, dermatitis (atopic dermatitis, chronic dermatitis, and such), inflammatory bowel diseases (colitis and such), asthma, arthritis (rheumatoid arthritis, osteoarthritis, and such), bronchitis, Th2 autoimmune diseases, systemic lupus erythematosus, myasthenia gravis, chronic GVHD, Crohn's disease, spondylitis deformans, lumbar pain, gout, inflammation after surgery or injury, swelling, neuralgia, laryngopharyngitis, cystitis, hepatitis (non-alcoholic steatohepatitis, alcoholic hepatitis, and such), hepatitis B, hepatitis C, and arteriosclerosis.

Preferred examples of inflammatory diseases that are subjects of the present invention include atopic dermatitis, chronic dermatitis, rheumatism, osteoarthritis, and chronic asthma.

The present inventors discovered that NR 10 antagonist antibodies have therapeutic effects against atopic dermatitis, chronic dermatitis, rheumatism, and osteoarthritis. On the other hand, it was revealed that NR 10 antagonist antibodies do not produce therapeutic effects in acute contact dermatitis and DSS acute colitis models.

The agents for preventing or treating inflammatory diseases of the present invention comprise as an active ingredient an NR 10 antagonist or an antibody having NR 10-neutralizing activity described above. The phrase "comprises an NR 10 antagonist as an active ingredient" means comprising an NR 10 antagonist as at least one of the active ingredients, and does not limit the contents. In addition, the agents for preventing or treating inflammatory diseases of the present invention may also comprise, in combination with an NR 10 antagonist, other ingredients that enhance the prevention or treatment of the inflammatory disease.

The NR 10 antagonist of the present invention can be formulated according to standard methods (see, for example, Remington's Pharmaceutical Science, latest edition, Mark Publishing Company, Easton, USA). Further, they may comprise pharmaceutically acceptable carriers and/or additives if necessary. For example, they may contain surfactants (for example, PEG and Tween), excipients, antioxidants (for example, ascorbic acid), coloring agents, flavoring agents, preservatives, stabilizers, buffering agents (for example, phosphoric acid, citric acid, and other organic acids), chelating agents (for example, EDTA), suspending agents, isotonizing agents, binders, disintegrators, lubricants, fluidity promoters, and corrigents. However, the carriers that can be comprised in the agents for preventing or treating inflammatory diseases of the present invention are not limited to this list. In fact, other commonly used carriers such as light anhydrous silicic acid, lactose, crystalline cellulose, mannitol, starch, carmelose calcium, carmelose sodium, hydroxypropylcellulose, hydroxypropylmethylcellulose, polyvinylacetaldiethylaminoacetate, polyvinylpyrrolidone, gelatin, medium chain fatty acid triglyceride, polyoxyethylene hydrogenated castor oil 60, sucrose, carboxymethylcellulose, corn starch, inorganic salt, and so on, can be appropriately comprised. The compositions may also comprise other low-molecular-weight polypeptides, proteins such as serum albumin, gelatin, and immunoglobulin, and amino acids such as glycine, glutamine, asparagine, arginine, and lysine. When the composition is prepared as an aqueous solution for injection, NR 10 antagonists may be dissolved in an isotonic solution comprising, for example, physiological saline, dextrose, and other adjuvants. The adjuvants may include, for example, D-sorbitol, D-mannose, D-mannitol, and sodium chloride. In addition, appropriate solubilizing agents, for example, alcohols (for example, ethanol), polyalcohols (for example, propylene glycols and PEGs), and non-ionic detergents (polysorbate 80 and HCO-50) may be used concomitantly.

If necessary, NR 10 antagonists may be encapsulated in microcapsules (microcapsules made of hydroxycellulose, gelatin, polymethylmethacrylate, and the like), and made into components of colloidal drug delivery systems (liposomes, albumin microspheres, microemulsions, nano-particles, and nano-capsules) (for example, see "Remington's Pharmaceutical Science 16th edition" &, Oslo Ed. (1980)). Moreover, methods for making sustained-release drugs are known, and these can be applied for NR 10 antagonists (Langer et al., J. Biomed. Mater. Res. (1981) 15, 167-277; Langer, Chem. Tech. (1982) 12, 98-105; U.S. Pat. No. 3,773,919; European Patent Application (EP) No. 58,481; Sidman et al., Biopolymers (1983) 22, 547-56 ; EP 133,988).

The agents for preventing or treating inflammatory diseases of the present invention can be administered either orally or parenterally, but are preferably administered parenterally. Specifically, the agents are administered to patients by injection or percutaneous administration. Injections include, for example, intravenous injections, intramuscular injections, and subcutaneous injections, for systemic or local administration. The agents may be given to sites where inflammation is to be suppressed, or areas surrounding the sites by local infusion, intramuscular injection in particular. The administration methods can be properly selected according to the patient's age and condition. The single-administration dose can be selected, for example, from within the range of 0.0001 to 100 mg of the active ingredient per kg body weight. Alternatively, when the agents are administered to human patients, the dose of the active ingredient can be selected from within the range of 0.001 to 1,000 mg/kg body weight. The single-administration dose preferably comprises, for example, NR 10 antagonist at about 0.01 to 50 mg/kg body weight. However, the dose of an agent for preventing or treating inflammatory diseases of the present invention is not limited to these examples.

The present invention also provides antibodies having NR 10-neutralizing activity (including fragments of antibodies having NR 10-neutralizing activity, and/or modification products thereof, the same definition is used throughout the description below). The antibodies having NR 10-neutralizing activity of the present invention are useful as active ingredients in the above-described agents for preventing or treating inflammatory diseases. The antibodies having NR 10-neutralizing activity of the present invention may be polyclonal or monoclonal antibodies, but are preferably monoclonal antibodies. Such monoclonal antibodies having NR 10-neutralizing activity can be obtained by the methods described above. The monoclonal antibodies of the present invention have the activity of neutralizing NR 10 derived from mammals or fragments thereof, preferably have the activity of neutralizing NR 10 derived from humans or mice, or fragments thereof, and more preferably the activity of neutralizing NR 10 derived from humans or fragments thereof. Human NR 10 or a peptide fragment thereof may be used as an immunogen to prepare monoclonal antibodies having the activity of neutralizing human NR 10. Alternatively, the antibodies having NR 10-neutralizing activity of the present invention may be recombinant antibodies. Recombinant antibodies having NR 10-neutralizing activity of the present invention include, but are not limited to, chimeric antibodies, humanized antibodies, human antibodies, and minibodies.

In the present invention, the antibodies having NR 10-neutralizing activity include, for example, anti-mouse NR 10 antibodies that comprise a heavy chain variable region comprising the amino acid sequence of SEQ ID NO: 1 and a light chain variable region comprising the amino acid sequence of SEQ ID NO: 3.

The present invention also includes monoclonal antibodies having the activity of neutralizing human NR 10. The monoclonal antibodies having the activity of neutralizing human NR 10 of the present invention can be obtained by preparing monoclonal antibodies using human NR 10 or a peptide fragment thereof as an immunogen, and then selecting from the anti-human NR 10 monoclonal antibodies, antibodies that have the activity of neutralizing human NR 10, based on the above-described assay system using the IL-31-dependent cell line.

In the present invention, the antibodies having the activity of neutralizing human NR 10 include the antibodies described in any one of:
(a) antibodies having a heavy chain variable region comprising CDR1, CDR2, and CDR3 that consist of the amino acid sequences of SEQ ID NOs: 18, 19, and 20, respectively.
(b) antibodies having a light chain variable region comprising CDR1, CDR2, and CDR3 that consist of the amino acid sequences of SEQ ID NOs: 21, 22, and 23, respectively;
(c) antibodies having the heavy chain variable region of (a) and the light chain variable region of (b); and
(d) antibodies that recognize the same epitope as that recognized by the antibodies of any one of (a) to (c).

Whether an antibody recognizes the same epitope as that recognized by another antibody can be confirmed by the competition between the two antibodies against the epitope. Competition between the antibodies can be evaluated by competitive binding assays using means such as ELISA, fluorescence energy transfer method (FRET), and fluorometric microvolume assay technology (FMAT(R)). The amount of antibodies bound to an antigen indirectly correlate with the binding ability of candidate competitor antibodies (test antibodies) that competitively bind to the same epitope. In other words, as the amount of or the affinity of test antibodies against the same epitope increases, the amount of antibodies bound to the antigen decreases, and the amount of test antibodies bound to the antigen increases. Specifically, appropriately labeled antibodies and antibodies to be evaluated are simultaneously added to the antigens, and the thus bound antibodies are detected using the label. The amount of antibodies bound to the antigen can be easily determined by labeling the antibodies beforehand. This label is not particularly limited, and the labeling method is selected according to the assay technique used. The labeling method includes fluorescent labeling, radiolabeling, enzymatic labeling, and such.

For example, fluorescently labeled antibodies and unlabeled antibodies or test antibodies are simultaneously added to animal cells expressing NR 10, and the labeled antibodies are detected by fluorometric microvolume assay technology.

$IC_{50}$ is the concentration in which the amount of labeled antibodies bound to the epitope is reduced to 50% by the binding of unlabeled antibodies. Herein, antibodies that recognize the same epitope are antibodies that can reduce the amount of labeled antibodies bound to the epitope to at least 50% when the concentration of test antibodies is ten times higher than the $IC_{50}$ of the unlabeled antibodies.

Antibodies having the activity of neutralizing human NR 10 that are used in the present invention preferably further have binding activity to cynomolgus monkey NR 10, and more preferably have the activity of neutralizing cynomolgus monkey NR 10. The cynomolgus monkey NR 10 comprising the amino acid sequence of SEQ ID NO: 24 can be used in measurements of the activity of neutralizing or binding to cynomolgus monkey NR 10.

The present invention also provides the therapeutic methods described below. The interpretation of NR 10, antagonists, monoclonal antibodies, recombinant antibodies, inflammatory diseases, and others in the methods are as described above.

(1) a method for preventing or treating an inflammatory disease, which comprises the step of administering an NR 10 antagonist to a patient with an inflammatory disease;
(2) the method of (1), in which the NR 10 antagonist is an antibody having the activity of binding to NR 10;
(3) the method of (2), in which the antibody is a monoclonal antibody;
(4) the method of (2), in which the antibody is a monoclonal antibody that binds to human NR 10; (5) the method of any one of (2) to (4), in which the antibody is a recombinant antibody;
(6) the method of (5), in which the recombinant antibody is a chimeric antibody, humanized antibody, or human antibody;
(7) the method of any one of (2) to (6), in which a fragment of an antibody having NR 10-neutralizing activity and/or a modified product thereof are included as an active ingredient;
(8) the method of any one of (1) to (7), in which the inflammatory disease is atopic dermatitis;
(9) the method of any one of (1) to (7), in which the inflammatory disease is chronic dermatitis;
(10) the method of any one of (1) to (7), in which the inflammatory disease is rheumatism; and
(11) the method of any one of (1) to (7), in which the inflammatory disease is osteoarthritis.

The present invention also provides the inventions described below. The explanation of NR 10, antagonists, monoclonal antibodies, recombinant antibodies, inflammatory diseases, and others in the methods are as described above.

(1) use of an NR 10 antagonist to produce an agent for preventing or treating an inflammatory disease;
(2) the use of (1), in which the NR 10 antagonist is an antibody having the activity of binding to NR 10;
(3) the use of (2), in which the antibody is a monoclonal antibody;
(4) the use of (2), in which the antibody is a monoclonal antibody that binds to human NR 10;
(5) the use of any one of (2) to (4), in which the antibody is a recombinant antibody;
(6) the use of (5), in which the recombinant antibody is a chimeric antibody, humanized antibody, or human antibody;
(7) the use of any one of (2) to (6), in which a fragment of an antibody having NR 10-neutralizing activity and/or a modification product thereof are included as an active ingredient;
(8) the use of any one of (1) to (7), in which the inflammatory disease is atopic dermatitis;
(9) the use of any one of (1) to (7), in which the inflammatory disease is chronic dermatitis;
(10) the use of any one of (1) to (7), in which the inflammatory disease is rheumatism; and
(11) the use of any one of (1) to (7), in which the inflammatory disease is osteoarthritis.

All prior-art documents cited herein are incorporated by reference herein.

EXAMPLES

Herein below, the present invention will be specifically described with reference to Examples, but it is not to be construed as being limited thereto.

Example 1

Establishment of Ba/F3 Cell Line that Express NR 10 and OSMR

A human NR 10 cDNA (SEQ ID NO: 1 of WO 0075314) was inserted into the expression vector pCOS1 (Biochem Biophys Res Commun. 228, p 838-45, 1996) to produce pCosNR 10.3. An oncostatin M receptor cDNA (OSMR, GenBank accession No. NM003999) was isolated from a human placental library by PCR, and then the expression vector pCos1-hOSMR was similarly constructed. By electroporation, 10 μg each of the vectors were simultaneously introduced into cells of the cell line Ba/F3 derived from mouse IL-3-dependent pro-B cells (BioRad Gene Pulser; 960 μF and 0.33 kV). After introduction, human IL-31 was added and the cells were cultured. Thus, a cell line that proliferated in an IL-31-dependent fashion was obtained. Likewise, a mouse-IL-31-dependent cell line was also prepared from Ba/F3 cells that were made to express the mouse NR 10 and OSMR genes.

In both cell lines, ED50 was found to be several ng/ml. Thus, well-proliferating cell lines were obtained. The human-IL-31-dependent cell line exhibited no response to mouse IL-31, and the growth was suppressed upon addition of human NR 10 protein (extracellular domain). The mouse-IL-31-dependent cell line exhibited no response to human IL-31, and the growth was not suppressed by the added mouse NR 10 protein (extracellular domain).

Example 2

Preparation of NR 10 Protein (Extracellular Domain)

The extracellular domain alone was amplified by PCR using NR 10 cDNA as a template, a FLAG tag sequence was attached to the C terminus, and was inserted into the expression vector pCXND3 (WO 2005/005636) (pCXND3-NR 10-flag). 10 μg of this linear vector was introduced into cells of Chinese hamster ovary cell line DG44 by electroporation (BioRad Gene PulserII; 25° F. and 1.5 kV). A high expression cell line was obtained. A purified sample was prepared from a supernatant of large-scale culture of the cell line by anti-FLAG antibody column (SIGMA) and gel filtration, and used in the experiments described below. Mouse NR 10 (extracellular domain) with FLAG tag sequence attached to the C terminus was similarly prepared.

Example 3

Isolation of scFv Having Anti-Mouse NR 10 Neutralizing Activity, and Preparation of BM095 as a Chimerized IgG Specifically, the present inventors tried to narrow down the candidate clones from a human antibody phage library by panning using biotinylated mouse NR 10 protein (extracellular domain). Secretory scFv were purified from the clones, and added to the cell growth assay system using IL-31-dependent Ba/F3 cells described in Example 1. As a result, the clone BM095 exhibiting strong growth-suppressing activity was successfully obtained.

Using PCR, the human H chain variable region (VH) sequence of BM095 was linked to mouse IgG2a constant region (after CHI), and human L chain variable region (VL) sequence of BM095 was linked to mouse λ chain constant region, to construct an expression vector. The amino acid sequence of the VH is shown in SEQ ID NO: 1, and the nucleotide sequence encoding the amino acid sequence is shown in SEQ ID NO: 2. The amino acid sequence of the VL is shown in SEQ ID NO: 3, and the nucleotide sequence encoding the amino acid sequence is shown in SEQ ID NO: 4. The respective linear expression vectors were simultaneously introduced into the cell line DG44, and then a cell line expressing chimerized IgG at a high level was selected. A purified sample was obtained from a supernatant of a large-scale culture of this cell line using a protein A (rProtein A Sepharose Fast Flow, GE Amersham Biosciences) column and cation-exchange column chromatography (SP-TOYO-PEARL 650M, TOSOH). Furthermore, pyrogen was removed using ActiClean Etox (Sterogen) resin to reduce the concentration to below the detection limit. The sample was used in the animal experiments described below. A result obtained by adding BM095 to the assay system described above is shown in FIG. 1.

Example 4

Assessment of Drug Efficacy in an Atopic Dermatitis Model Using NC/Nga Mice

A dermatitis model was produced by repeated application of picryl chloride (PiCl) at weekly intervals. Specifically, 4 days after sensitization with 5% PiCl (150 μl) on the abdomen and footpad, the induction of dermatitis was achieved by repeated application of 0.8% PiCl (150 μl) on the back and auricle at weekly intervals. The resulting symptoms were observed twice a week over the third to sixth week period, and five perspectives ((1) pruritus, (2) redness and bleeding, (3) edema, (4) injury and tissue damage, and (5) incrustation and dryness) were independently scored on a scale of 0 to 3. The antibody was administered at 10 mg/kg into the peritoneal cavities the day before sensitization and each induction, 6 times in total (BM095 group), or the day before each induction after the third week, three times in total (V/B group). As a positive control, 1 mg/kg dexamethasone was orally administered every day after the third week (DEX group). Each group contained 10 male NC/Nga mice.

Figure 2:
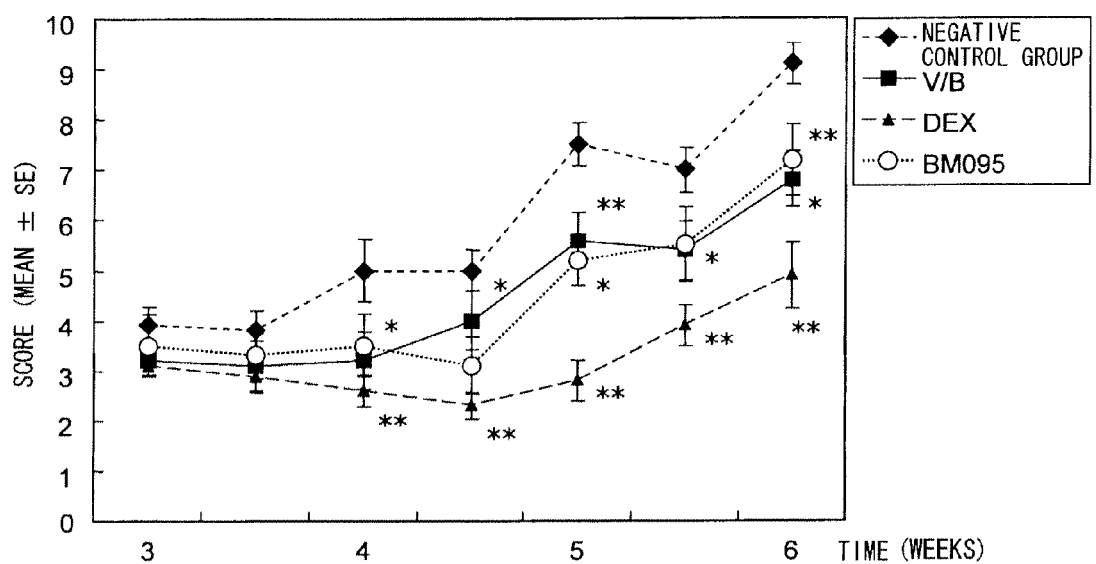
FIG. 2 is a graph showing a therapeutic effect produced when anti-NR 10 antibodies were administered to atopic dermatitis model mice. A significant inflammation-suppressing effect was seen in the anti-NR 10 antibody administered group as compared with the negative control group (vehicle group).
Figure 3:
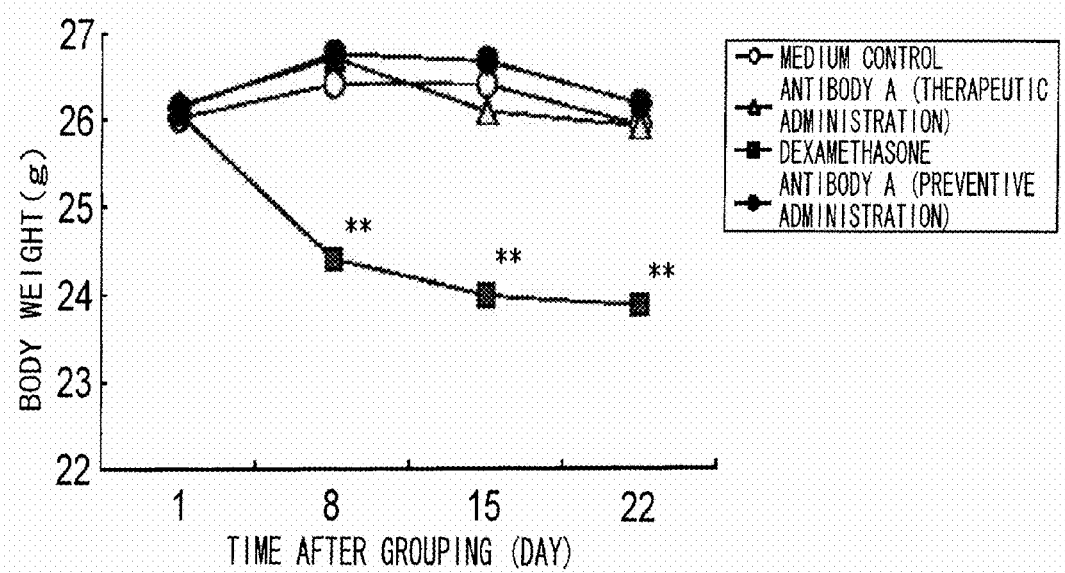
FIG. 3 is a graph showing a sequential change in body weight after anti-NR 10 antibodies were administered to atopic dermatitis model mice. Weight loss was observed in the group administered with an existing anti-inflammatory agent. In contrast, no weight change was detected in the anti-NR 10 antibody-administered group. Thus, the anti-NR 10 antibody was proven to be safe.

As shown in FIG. 2, a significant suppressive effect was found in the antibody-administered group as compared to the solvent-administered vehicle group. In addition, as seen in FIG. 2, whereas significant weight loss was found in the DEX group, there was no weight change in the antibody-administrated group. This suggests that the antibody is a very safe agent.

Example 5

Assessment of Drug Efficacy Using a Chronic Dermatitis Model Created by Repeated Application of Picryl Chloride Six-week-old female BALB/c mice were sensitized by applying 20 μl of 0.5% picryl chloride (acetone/olive oil (1:4 v/v) solution) on their right ears. The induction was achieved by repeatedly applying 20 μl of 0.25% picryl chloride (acetone/olive oil (1:4 v/v)) on their right ears every two days since the eighth day after sensitization. 10 mg/kg of BM095 was administered into the peritoneal cavities once a week since the day before sensitization in the group for evaluation of the preventive effect of BM095 or since the 20th day after the start of induction in the group for evaluation of the therapeutic effect of BM095. Auricle swelling was evaluated by sequentially measuring the thickness of right ear using a dial thickness gauge.

Figure 4:
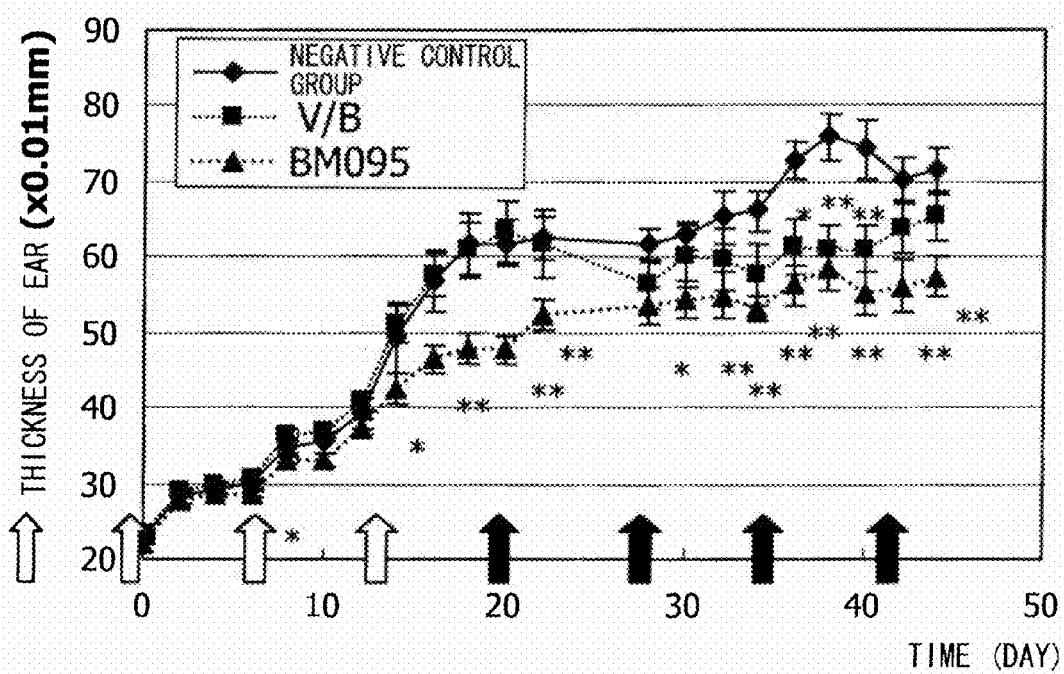
FIG. 4 is a graph showing a therapeutic effect produced when anti-NR 10 antibodies were administered to chronic dermatitis model mice. A significant auricle swelling-suppressing effect was found in the anti-NR 10 antibody-administered group.
Figure 5:
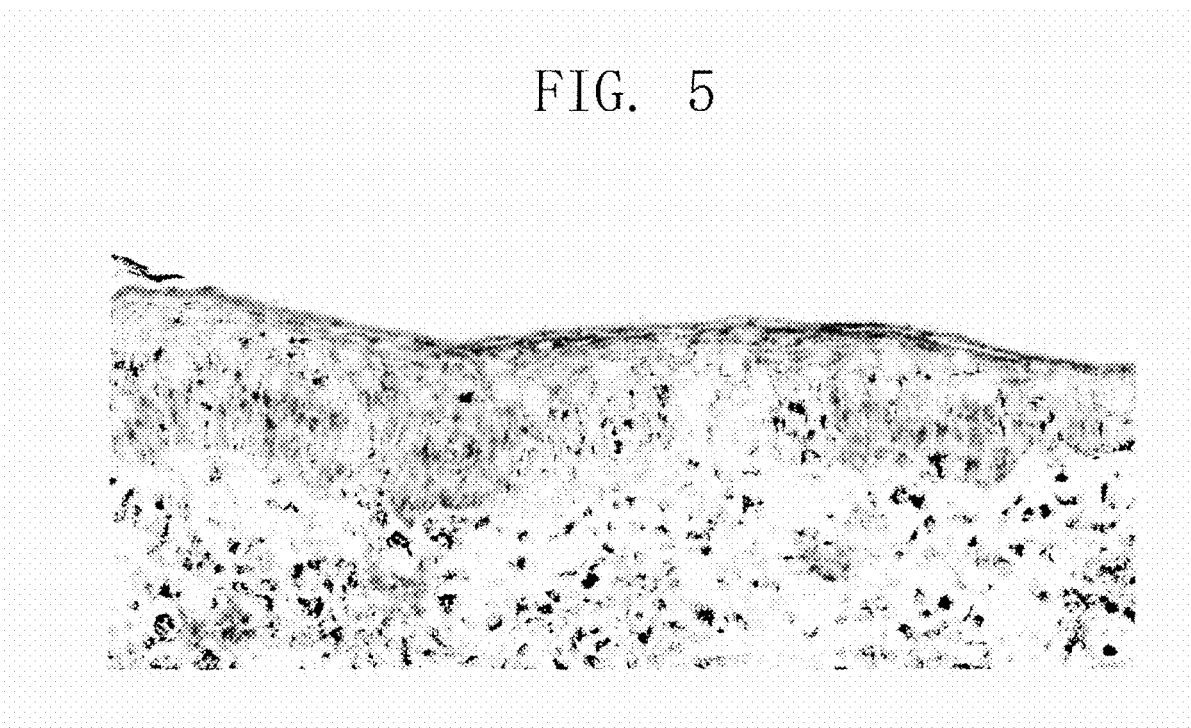
FIG. 5 is a photograph showing immunohistochemical staining of the auricle of a chronic dermatitis model mouse. As with the case of humans, the expression of mouse NR 10 was found to be enhanced in thickened epidermis.

As a result, a significant suppressive effect was found in the antibody-administered group, as seen in FIG. 4. The expression of human NR 10 was reported to be enhanced in thickened epidermis of atopic dermatitis patients (Non-patent Document 1). Auricles of the above-described chronic dermatitis model mice were immunohistochemically stained. As with the case of humans, the expression of mouse NR 10 was observed to be enhanced in the thickened epidermis (FIG. 5; BM095 in which the constant region was replaced with that of human IgG was prepared in Example 3 and used in immunohistochemical staining. Portions stained brown are NR 10 expression sites). This finding suggests that NR 10 is similarly involved in inflammatory diseases in both human and mouse.

Example 6

Assessment of Drug Efficacy Using Collagen-Induced Arthritis (Rheumatism) Model Preparation of model mice and evaluation of drug efficacy were achieved by the procedure described below.

140 μl of collagen gel, which was prepared by combining equal amounts of Complete Adjuvant H37Ra and 0.3% type II collagen derived from bovine joint, was administered intracutaneously to 9-week old female DBA/1JN mice at the tail head (Day 0; sensitization). After three weeks, collagen gel prepared by the same procedure was administered intracutaneously on the back to induce the onset of arthritis (Day 21;

induction). According to the body weights two days before sensitization (Day −2), 16 mice were divided into two groups, each including 8 mice, to set a medium-administered group and a BM095-administered group. Using as a medium 20 mmol/l acetate buffer (pH 5.5) (200 mmol/l NaCl) diluted 6 times with PBS, the test substance BM095 was administered intravenously to the 8 mice of the BM095-administered group at the dose of 10 mg/weight kg the day before sensitization (Day −1). Meanwhile, the same volume of the medium per unit body weight was administered to the 8 mice in the medium-administered group as a control on Day −1. Swelling in the four limbs was observed and evaluated by scoring (on a scale of 0 to 4 for each limb: total score 16) since the day before induction (Day 20) at 2- to 3-day intervals.

Figure 6:
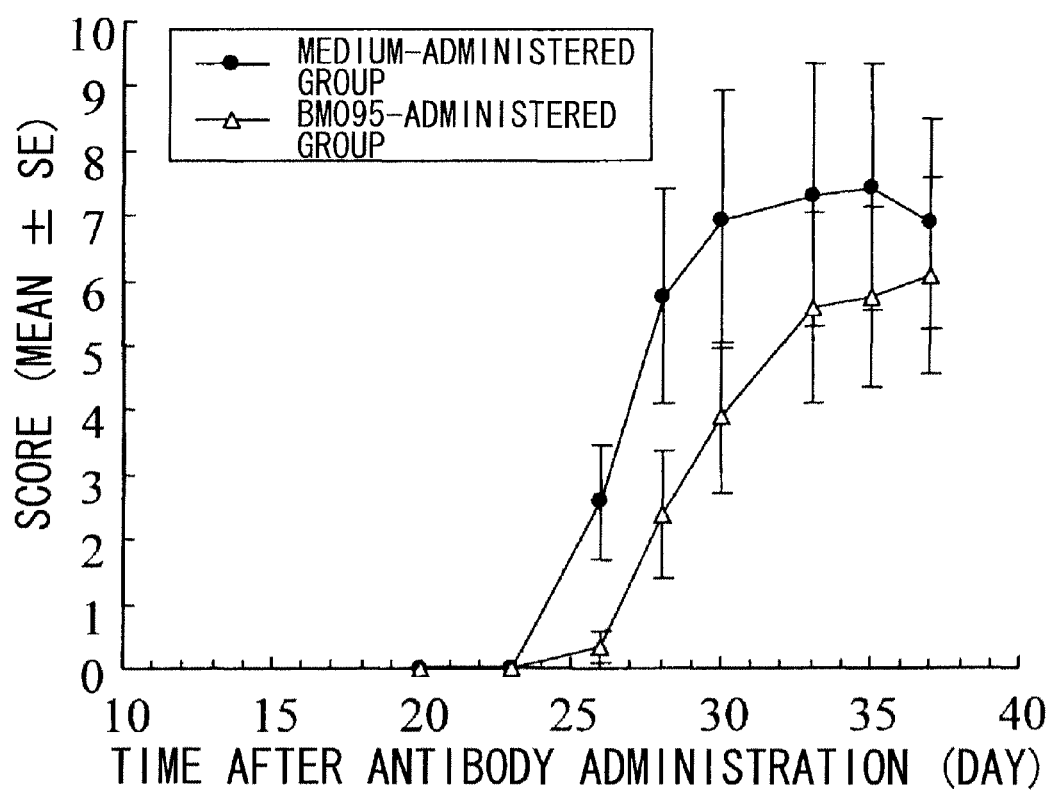
FIG. 6 is a graph showing an arthritis-suppressing effect produced when anti-NR 10 antibodies were administered to collagen-induced arthritis model mice.

As a result, the score for swelling in the four limbs was found to decrease after Day 20 in the BM095-administered group, as seen in FIG. 6. This suggests that BM095 has the effect of suppressing the onset of arthritis.

Example 7

Assessment of Drug Efficacy Using Collagenase-Induced Arthritis (Osteoarthritis) Model Preparation of Model Mice and Evaluation of Drug Efficacy were Achieved by the Procedure described below.

A control medium (20 mmol/l acetate buffer (pH 5.5) diluted 6 times with PBS, 200 mmol/l NaCl (n=5)), 2 mg/kg BM095 (n=5), and 20 mg/kg BM095 (n=6) were administered (5 ml/kg) intravenously into the caudal veins of 8-week-old male C57BL/6J Jcl mice (CLEA Japan Inc.). Then, 6 μl of 1.5% collagenase solution (Type II; Sigma) filtered through 0.45-μm filter (MILLIPORE) was administered into the right knee joint cavities under anesthesia with inhalation of 3% isoflurane (Am J Pathol 1989; 135(6):1001-14).

Figure 7:
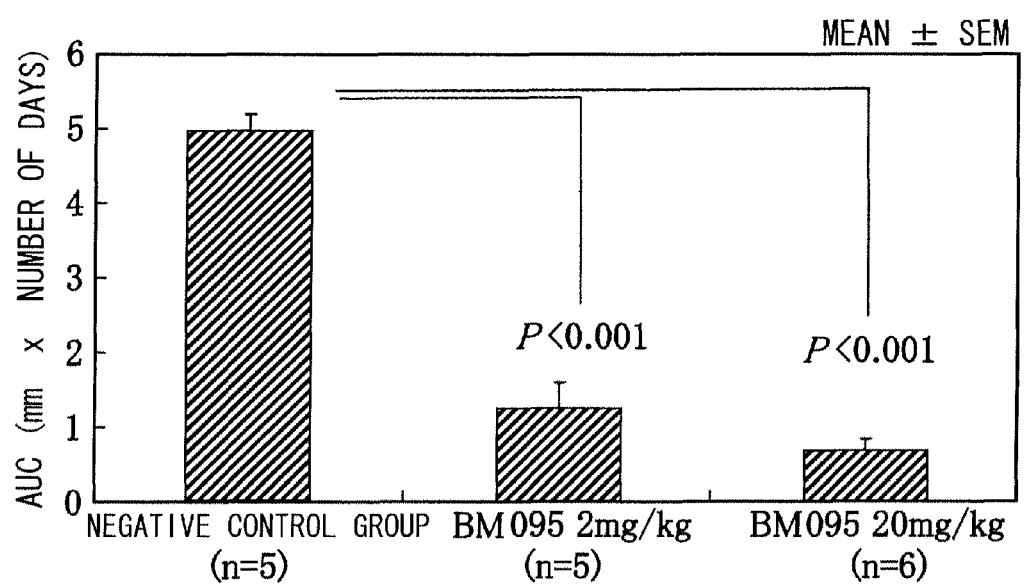
FIG. 7 is a graph showing the relationship between the area under the curve (AUC) and the concentration of BM095 administered to the collagenase-induced arthritis (osteoarthritis) model. AUC means the area under the curve of transition of the difference between the right and left knee joint widths defined as a value representing swelling in the right knee joint.

The widths of right and left knee joints were determined using calipers (Mitsutoyo CO.) immediately before collagenase administration and 3, 7, and 14 days after collagenase administration to calculate the difference between right and left. The difference was defined as a representative value for right knee joint swelling. The area under the curve (AUC) of transition of this difference was determined based on the trapezoidal rule, and defined as an indicator of drug efficacy. Student's t test was conducted for AUC of the medium control group and BM095-administered group using a statistical analysis software (SAS Institute Inc.) (a significant difference is assumed when p<0.05). As a result, AUC of the BM095-administered group was significantly smaller at any dose than that of the medium control group, as seen in FIG. 7. This result demonstrates that BM095 suppresses arthritis in the osteoarthritis model.

Example 8

Preparation of Anti-Human NR 10 Neutralizing Antibody

Figure 8:
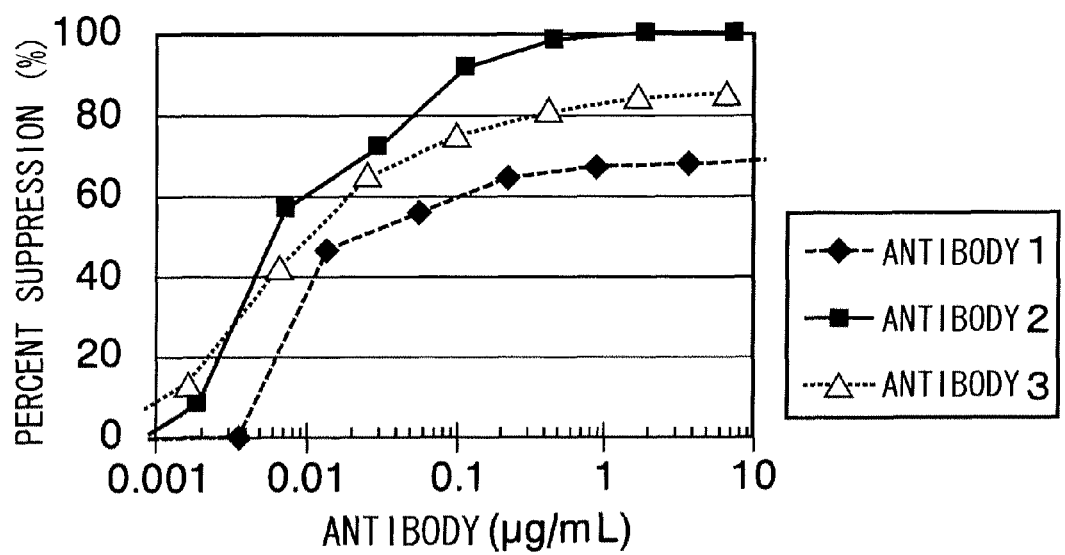
FIG. 8 is a graph showing the correlation between the concentration of human NR 10 neutralizing antibodies (purified antibody) and cell growth-suppressing activity in the presence of IL-31. Antibodies 1, 2, and 3 exhibited strong NR 10-neutralizing activity.

Mice were immunized with human NR 10 protein (extracellular domain) {described in Example 2}, and hybridomas were prepared by conventional methods. The culture supernatants of the hybridomas were assayed for the neutralizing activity using the human-IL-31-dependent cell line (hNR 10/hOSMR/BaF3 cells) described in Example 1. Multiple clones exhibiting strong NR 10 neutralizing activity were obtained (FIG. 8).

Example 9

Preparation of Human Chimeric Antibody

The amino acid sequence of the heavy chain variable region of NA633, which exhibited the strongest activity among neutralizing antibodies, is shown in SEQ ID NO: 16, and the amino acid sequence of the light chain variable region is shown in SEQ ID NO: 17. In addition, the amino acid sequences of CDR1, CDR2, and CDR3 of the heavy chain variable region of NA633 are shown in SEQ ID NOs: 18, 19, and 20, respectively; and the amino acid sequences of CDR1, CDR2, and CDR3 of the light chain variable region are shown in SEQ ID NOs: 21, 22, and 23, respectively.

Furthermore, a chimeric antibody comprising the above-described mouse variable region and human constant region (IgG1-type H chain; κ-type L chain) was prepared by a conventional method, and the neutralizing activity was determined. As shown in FIG. 9, the chimeric antibody NA633 exhibited strong neutralizing activity at low concentrations.

Example 10

Isolation of Cynomolgus Monkey NR 10

The inventors tried to isolate the cynomolgus monkey NR 10 gene, because the cross-reactivity and neutralizing activity to cynomolgus monkey NR 10 were thought to be important in safety assessment at the preclinical step. Primers were designed based on disclosed Rhesus monkey genomic information and such, and the NR 10 gene was successfully amplified from organs of cynomolgus monkey by PCR. An alignment of amino acid sequences of human NR 10 and the isolated cynomolgus monkey NR 10 is shown in FIG. 10. The amino acid sequence of the cynomolgus monkey NR 10 is shown in SEQ ID NO: 24. A cell line proliferating in a human-IL-31-dependent fashion was established by introducing the cynomolgus monkey NR 10 gene together with the human OSMR gene into Ba/F3 cells, as described in Example 1. The neutralizing activity of the chimeric antibody NA633 described in Example 9 was tested using this cell line. The result demonstrated that the antibody also exhibited strong neutralizing activity in cynomolgus monkey (FIG. 11).

Reference Example 1

Drug Efficacy of BM095 in Dextran Sulfate Sodium (DSS) Induced Colitis

DSS-induced colitis model (J Immunol (2003) 171:5507-5513), which was reported as a pathological model for inflammatory bowel disease (IBD), was prepared to evaluate the effect of BM095, an anti-mouse NR 10 neutralizing antibody. An aqueous solution of 5% (w/v) Dextran Sulfate Sodium Salt (Wako Pure Chemical Industries) was prepared using distilled water filtered and sterilized with 0.22-pm filter (Millipore). Six-week old male Balb/cAnN Crj mice (CHARLES RIVER LABORATORIES JAPAN) were allowed to freely drink the solution from water bottles for 7 days. The body weights were measured, and weight changes relative to the weights on the first day of DSS administration were used as an index of drug efficacy.

Using this model, the anti-mouse NR 10 neutralizing antibody BM095 was intravenously administered at a dose of 10 mg/kg the day before DSS administration and the resulting weight loss was evaluated (n=10) to test whether the pathological condition was improved by neutralizing IL-31 signaling. The group (Vehicle group; n=10) in which a vehicle (a mixture of acetate buffer [20 mmol/L sodium acetate and 20 mmol/L sodium chloride] and phosphate-buffered saline [PBS; GIBCO], which were mixed at a volume ratio of 1:5) was administered intravenously the day before DSS administration, was used as a vehicle control group. Furthermore, the course of weight change in Balb/cAnN Crj mice of same sex and age (n=1) as those in the DSS-administered group was also investigated to know the time course of weight change in normal mice.

The course of weight change (shown as a percent of starting weight) over seven days' time for all three groups is shown in FIG. 12. DSS administration caused a reduction in weight over time in the Vehicle group. The course of weight change in the BM095 administered group was similar to that in the Vehicle group. However, four and five days after DSS administration, the weight loss in the BM095 group was significantly greater than the weight loss in the Vehicle group. These results showed that the administration of BM095 produced no therapeutic effect on colitis of the model.

It has been reported that the expression of IL-31Ra is enhanced in this model (WO 2004/003140). The experimental results described above demonstrate that antibodies neutralizing the molecule produce no therapeutic effect on colitis of this model.

Reference Example 2

Drug Efficacy of BM095 in Picryl Chloride-Induced Acute Contact Dermatitis Model To evaluate the effect of the anti-mouse NR 10 neutralizing antibody BM095, a Dermatitis reported as an acute contact dermatitis model (Clin Immunol (2003) 108: 257-262) was developed. This Dermatitis is a result of a delayed hypersensitivity reaction due to sensitization and induction by picryl chloride application. 50 μL of a solution of 7% picryl chloride (nacalai tesque, Inc.; ethanol:acetone=3:1 (v/v)) was applied onto abdominal skin to sensitize 8-week old female Balb/cAnN Crj mice (CHARLES RIVER LABORATORIES JAPAN), and after 5 days, 20 μL of 1% picryl chloride solution (acetone:olive=1:4 (v/v)) was applied onto the skin of right auricles to elicit contact dermatitis (Induction). 20 μL of a vehicle (acetone:olive=1:4 (v/v)) was applied onto the skin of left auricles of the same mice as a control to evaluate the effect of the vehicle on the thickness of auricle (Positive group; n=6). The thicknesses of right and left ears were measured using a Dial Thickness Gauge (OZAKI MFG.) immediately before induction and 24, 48, and 72 hours after induction, and the change in the thickness of auricle relevant to the thickness immediately before induction was used as an index for drug efficacy.

The group (Negative group; n=6) in which an ethanol-acetone mixture (3:1 (v/v)) without picryl chloride was applied onto the abdominal skin at the time of sensitization, and after 5 days, 20 μL of 1% picryl chloride solution was applied onto the skin of right auricle and 20 μL of a vehicle (acetone:olive=1:4 (v/v)) was applied onto the skin of left auricle, was used as a control group to evaluate the establishment of pathological conditions.

The group (BM095 group; n=6), in which acute contact dermatitis was induced by the same method as that used for the above-described Positive group and then BM095 was administered intravenously at 10 mg/kg the days before sensitization and induction, and the group (Vehicle group; n=5) in which at the same timing a vehicle (acetate buffer [20 mmol/L sodium acetate and 20 mmol/L sodium chloride] and phosphate-buffered physiological saline [PBS; GIBCO], which were combined at a volume ratio of 1:5) was administered, was used to evaluate the effect of administration of anti-NR 10 antibodies on the pathological conditions in the model system.

Figure 13:
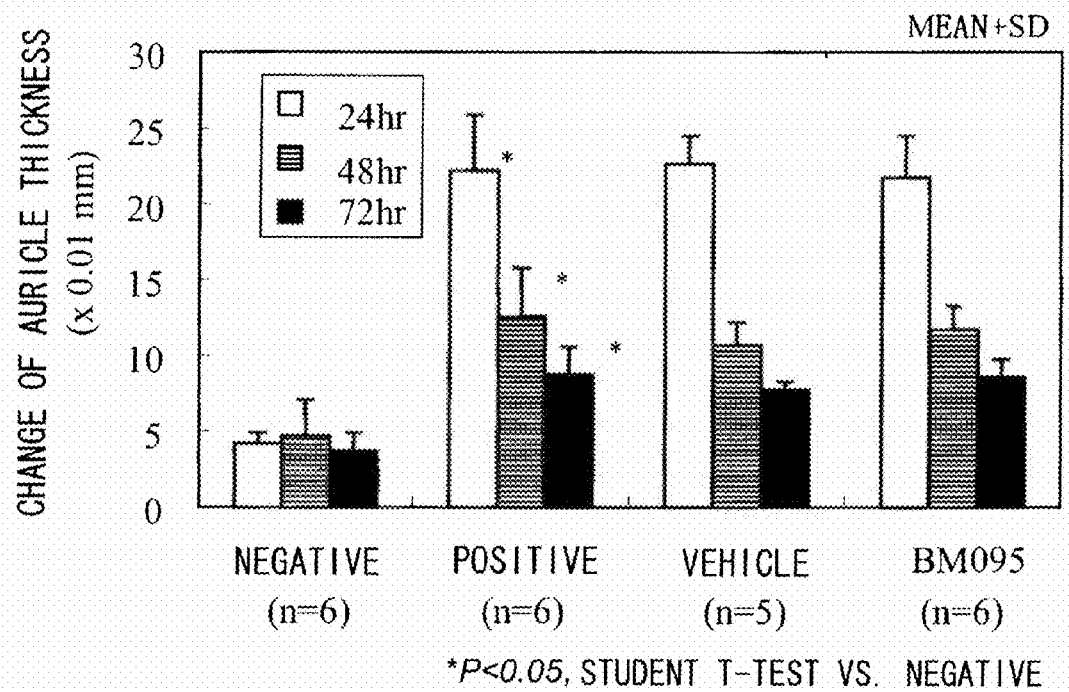
FIG. 13 is a graph showing the transition of change in the thickness of the auricle in the acute contact dermatitis model using picryl chloride.

The changes in auricle thickness up to 72 hours after induction are shown in FIG. 13. The auricle was found to be significantly thickened in the Positive group at each time point of 24, 48, and 72 hours after induction as compared to the Negative group, suggesting establishment of pathological conditions. The transition of auricle thickness in the BM095 group was similar to that in the Vehicle group, and thus, no significant suppression was found.

The results described above demonstrate that the administration of BM095 produce no therapeutic effect on acute contact dermatitis observed in this model.

INDUSTRIAL APPLICABILITY

The present invention provides novel agents for preventing or treating inflammatory diseases. The agents for preventing or treating inflammatory diseases provided by the present invention comprise as an active ingredient an NR 10 antagonist, more preferably, an antibody having NR 10-neutralizing activity.

Monoclonal antibody-based anti-cytokine therapy is drawing much attention in recent years. In many actual pathological conditions, however, it has been difficult to produce therapeutic effects by blocking a single cytokine, because compensatory pathways are activated. Further, it was difficult to estimate in what type of diseases therapeutic effects could be obtained by blocking the target cytokine. Under the circumstance described above, the present inventors discovered that anti-NR 10 neutralizing antibodies could significantly suppress symptoms in model mice with atopic dermatitis, chronic dermatitis, rheumatism, osteoarthritis or such.

The present inventors also succeeded in preparing human NR 10 neutralizing antibodies. Agents for preventing or treating inflammatory diseases, which comprise as an active ingredient human NR 10 neutralizing antibodies, are highly useful for clinical application to humans.

The invention claimed is:

1. A method for treating an inflammatory disease, the method comprising:
    administering an antibody that binds a novel cytokine receptor 10 (NR 10) and has an NR 10-neutralizing activity to a patient with an inflammatory disease; and
    assessing whether the patient's inflammatory disease is suppressed,
    wherein the antibody binds to and neutralizes human NR 10 and cynomolgus monkey NR 10, and
    wherein the inflammatory disease is atopic dermatitis, chronic dermatitis, rheumatism, osteoarthritis, or rheumatoid arthritis, provided that, when the inflammatory disease is atopic dermatitis, the assessment comprises assessing at least one of the following symptoms of atopic dermatitis: (a) pruritus, (b) redness, (c) bleeding, (d) edema, (e) tissue damage, (f) incrustation, and (g) dryness.

2. The method of claim 1, wherein the antibody is a monoclonal antibody.

3. The method of claim 1, wherein the antibody is a recombinant antibody.

4. The method of claim 1, wherein the antibody is a chimeric antibody, humanized antibody, or human antibody.

5. The method of claim 1, wherein the antibody is conjugated to a substance selected from the group consisting of polyethylene glycol, a radioactive substance, a fluorescent substance, a luminescent substance, an enzyme, and a toxin.

6. The method of claim 1, wherein the inflammatory disease is atopic dermatitis.

7. The method of claim 1, wherein the inflammatory disease is chronic dermatitis.

8. The method of claim 1, wherein the inflammatory disease is rheumatism.

9. The method of claim 1, wherein the inflammatory disease is osteoarthritis.

10. The method of claim 1, wherein the inflammatory disease is rheumatoid arthritis.

11. A method for treating an inflammatory disease, the method comprising administering a human or humanized antibody that binds a novel cytokine receptor 10 (NR 10) and has an NR 10-neutralizing activity to a patient with an inflammatory disease, wherein the antibody binds to and neutralizes human NR 10 and cynomolgus monkey NR 10, and wherein the inflammatory disease is atopic dermatitis, chronic dermatitis, rheumatism, osteoarthritis, or rheumatoid arthritis.

12. The method of claim 11, wherein the antibody has no therapeutic effect in preventing weight loss over seven days when tested in an experiment using a DSS-induced colitis mouse model, the experiment being carried out as follows: either the antibody at a dose of 10 mg/kg or a vehicle control (the vehicle being a mixture of one volume of 20 mmol/L sodium acetate/20 mmol/L sodium chloride, and five volumes of phosphate-buffered saline) is intravenously administered to six-week old male Balb/cAnN Crj mice on day zero; on days one through seven, both treated and vehicle control mice are allowed to drink freely an aqueous solution of 5% (w/v) DSS, and their weights are measured each day.

13. The method of claim 11, wherein the antibody does not produce a therapeutic effect on auricle thickness due to acute contact dermatitis when tested in an experiment using an acute contact dermatitis mouse model, where acute contact dermatitis is induced in the mouse model as follows:
    (i) measuring the thickness of a mouse's left and right auricles;
    (ii) applying 50 μl of 7% picryl chloride onto abdominal skin of the mouse;
    (iii) five days after step (ii), applying 20 μl of 1% picryl chloride prepared in acetone:olive 1:4 v/v to the skin of the right auricle and applying 20 μl of acetone:olive 1:4 v/v to the skin of the left auricle; and
    (iv) measuring the thickness of the left and right auricles 24, 48, and 72 hours after step (iii),
    wherein the experiment comprises intravenously administering 10 mg/kg of the antibody to the mouse on the day before step (ii) and again on the day before step (iii).

14. A method for treating an inflammatory disease, the method comprising:
administering an antibody that binds a novel cytokine receptor 10 (NR 10) and has an NR 10-neutralizing activity to a patient with an inflammatory disease; and
assessing whether the patient's inflammatory disease is suppressed, wherein the inflammatory disease is atopic dermatitis, chronic dermatitis, rheumatism, osteoarthritis, or rheumatoid arthritis, provided that, when the inflammatory disease is atopic dermatitis, the assessment comprises assessing at least one of the following symptoms of atopic dermatitis: (a) pruritus, (b) redness, (c) bleeding, (d) edema, (e) tissue damage, (f) incrustation, and (g) dryness, and
wherein the antibody is an antibody that has no therapeutic effect in preventing weight loss over seven days when tested in an experiment using a dextran sulfate sodium (DSS)-induced colitis mouse model, the experiment being carried out as follows: either the antibody at a dose of 10 mg/kg or a vehicle control (the vehicle being a mixture of one volume of 20 mmol/L sodium acetate/20 mmol/L sodium chloride, and five volumes of phosphate-buffered saline) is intravenously administered to six-week old male Balb/cAnN Crj mice on day zero; on days one through seven, both treated and vehicle control mice are allowed to drink freely an aqueous solution of 5% (w/v) DSS, and their weights are measured each day.

15. The method of claim 14, wherein the antibody binds to and neutralizes human NR 10 and cynomolgus monkey NR 10.

16. A method for treating an inflammatory disease, the method comprising:
administering an antibody that binds a novel cytokine receptor 10 (NR 10) and has an NR 10-neutralizing activity to a patient with an inflammatory disease; and
assessing whether the patient's inflammatory disease is suppressed, wherein the inflammatory disease is atopic dermatitis, chronic dermatitis, rheumatism, osteoarthritis, or rheumatoid arthritis, provided that, when the inflammatory disease is atopic dermatitis, the assessment comprises assessing at least one of the following symptoms of atopic dermatitis: (a) pruritus, (b) redness, (c) bleeding, (d) edema, (e) tissue damage, (f) incrustation, and (g) dryness, and
wherein the antibody is an antibody that has no therapeutic effect on changes in auricle thickness due to acute contact dermatitis when tested in an experiment using an acute contact dermatitis mouse model, where acute contact dermatitis is induced in the mouse model as follows:
(i) measuring the thickness of a mouse's left and right auricles;
(ii) applying 50 µl of 7% picryl chloride onto abdominal skin of the mouse;
(iii) five days after step (ii), applying 20 µl of 1% picryl chloride prepared in acetone:olive 1:4 v/v to the skin of the right auricle and applying 20 µl of acetone:olive 1:4 v/v to the skin of the left auricle; and
(iv) measuring the thickness of the left and right auricles 24, 48, and 72hours after step (iii),
wherein the experiment comprises intravenously administering 10 mg/kg of the antibody to the mouse on the day before step (ii) and again on the day before step (iii).

17. The method of claim 16, wherein the antibody binds to and neutralizes human NR 10 and cynomolgus monkey NR 10.

18. A method for treating an inflammatory disease, the method comprising
administering a minibody or an antigen-binding fragment of a monoclonal antibody that binds a novel cytokine receptor 10 (NR 10) and has an NR 10-neutralizing activity to a patient with an inflammatory disease; and
assessing whether the patient's inflammatory disease is suppressed,
wherein the minibody or antigen-binding fragment binds to and neutralizes human NR 10 and cynomolgus monkey NR 10,
wherein the inflammatory disease is atopic dermatitis, chronic dermatitis, rheumatism, osteoarthritis, or rheumatoid arthritis, and
wherein, when the inflammatory disease is atopic dermatitis, the assessment comprises assessing at least one of the following symptoms of atopic dermatitis: (a) pruritus, (b) redness, (c) bleeding, (d) edema, (e) tissue damage, (f) incrustation, and (g) dryness.

19. A method for treating an inflammatory disease, the method comprising administering a minibody or an antigen-binding fragment of a monoclonal antibody that binds a novel cytokine receptor 10 (NR 10) and has an NR 10-neutralizing activity to a patient with an inflammatory disease, wherein the minibody or antigen-binding fragment binds to and neutralizes human NR 10 and cynomolgus monkey NR 10, and wherein the inflammatory disease is atopic dermatitis, chronic dermatitis, rheumatism, osteoarthritis, or rheumatoid arthritis.

20. A method for treating an inflammatory disease, the method comprising
identifying an antibody known to have human novel cytokine receptor 10 (NR 10) neutralizing activity and cynomolgus monkey NR 10-neutralizing activity; and
administering the antibody to a patient identified as having an inflammatory disease, wherein the inflammatory disease is atopic dermatitis, chronic dermatitis, rheumatism, osteoarthritis, or rheumatoid arthritis.

* * * * *